US012319942B2

(12) United States Patent
Liu et al.

(10) Patent No.: US 12,319,942 B2
(45) Date of Patent: Jun. 3, 2025

(54) USE OF MUTANT OF IMMUNOGLOBULIN DEGRADING ENZYME IDEE

(71) Applicant: SHANGHAI BAO PHARMACEUTICALS CO., LTD., Shanghai (CN)

(72) Inventors: Yanjun Liu, Shanghai (CN); Zheng Wang, Shanghai (CN); Zhen Zhu, Shanghai (CN); Lin Lu, Shanghai (CN)

(73) Assignee: SHANGHAI BAO PHARMACEUTICALS CO., LTD., Shanghai (CN)

( * ) Notice: Subject to any disclaimer, the term of this patent is extended or adjusted under 35 U.S.C. 154(b) by 0 days.

(21) Appl. No.: 18/749,788

(22) Filed: Jun. 21, 2024

(65) Prior Publication Data
US 2024/0336908 A1    Oct. 10, 2024

Related U.S. Application Data

(63) Continuation of application No. PCT/CN2022/141001, filed on Dec. 22, 2022.

(30) Foreign Application Priority Data

Dec. 22, 2021 (CN) .......................... 202111577633.5

(51) Int. Cl.
C12N 9/50 (2006.01)
A61K 38/48 (2006.01)
A61P 37/06 (2006.01)
C12N 9/52 (2006.01)

(52) U.S. Cl.
CPC ............. *C12N 9/52* (2013.01); *A61K 38/48* (2013.01); *A61P 37/06* (2018.01)

(58) Field of Classification Search
CPC .......... A61P 31/04; A61P 35/04; C12P 21/02; C07K 16/22; C07K 2319/30; C07K 16/00; C12Y 304/2201; C12Y 304/22
USPC ...................................................... 424/94.6
See application file for complete search history.

(56) References Cited

FOREIGN PATENT DOCUMENTS

| CN | 101232900 A | 7/2008 |
|---|---|---|
| CN | 102026658 A | 4/2011 |
| CN | 107532156 A | 1/2018 |
| WO | 2021254479 A1 | 12/2021 |

OTHER PUBLICATIONS

Kisselev L., (Structure, 2002, vol. 10: 8-9.*
Witkowski et al., (Biochemistry 38:11643-11650, 1999.*
Whisstock et al., (Quarterly Reviews of Biophysics 2003, vol. 36 (3): 307-340.*
Devos et al., (Proteins: Structure, Function and Genetics, 2000, vol. 41: 98-107.*
Jonas Lannerg, et al., IdeE, an IgG-endopeptidase of *Streptococcus equi* ssp.*equi*, FEMS Microbiol Lett, 2006, pp. 230-235, vol. 262.
WP_012515503.1, IgG-degrading enzyme/Mac-I IdeZ [*Streptococcus equi*], National Library of Medicine, 2013.
WP_012678049.1, IgG endopeptidase [*Streptococcus equi*], National Library of Medicine, 2013.
Mengyao Liu, et al., IgG Endopeptidase SeMac does not Inhibit Opsonophagocytosis of *Streptococcus equi* Subspecies *equi* by Horse Polymorphonuclear Leukocytes, The Open Microbiology Journal, 2010, pp. 20-25, vol. 4.
Johnson Agniswamy, et al., Insight of Host Immune Evasion Mediated by Two Variants of Group A *Streptococcus* Mac Protein, The Journal of Biological Chemistry, 2004, pp. 52789-52796, vol. 279 No. 50.
Benfang Lei, et al., Opsonophagocytosis-Inhibiting Mac Protein of Group A *Streptococcus*: Identification and Characteristics of Two Genetic Complexes, Infection and Immunity, 2002, pp. 6880-6890, vol. 70 No. 12.
Ulrich Von Pawel-Rammingen, et al., IdeS, a novel streptococcal cysteine proteinase with unique specifitiy for immunoglobulin G, The EMBO Journal, 2002, pp. 1607-1615, vol. 21 No. 7.
Ulrich Von Pawel-Rammingen, Streptococcal IdeS and Its Impact on Immune Response and Inflammation, J Innate Immun, 2012, pp. 132-140, vol. 4.
Jonas Lannergard, IdeE, an IgG-endopeptidase of *Streptococcus equi* ssp.*equi*, FEMS Microbiol Lett, 2006, pp. 230-235, vol. 262.
William F. Dall'Acqua, et al., Increasing the Affinity of a Human IgG1 for the Neonatal Fc Receptor: Biological Consequences, The Journal of Immunology, 2002, pp. 5171-5180.
Chang-Han Lee, et al., An engineered human Fc domain that behaves like a pH-toggle switch for ultra-long circulation persistence, Nature Communications, 2019, pp. 1-11, vol. 10, 5031.
Lu Shan, et al., Generation and Characterization of an IgG4 Monomeric Fc Platform, Plos One, 2016, pp. 1-18, vol. 11 No. 8.
Brian C. Mackness, et al., Antibody Fc engineering for enhanced neonatal Fc receptor binding and prolonged circulation halflife, mAbs, 2019, pp. 1276-1288, vol. 11 No. 7.
Christophe Dumet, et al., Insights into the IgG heavy chain engineering patent landscape as applied to IgG4 antibody development, mAbs, 2019, pp. 1341-1350, vol. 11 No. 8.
Xinhua Wang, et al., IgG Fc engineering to modulate antibody effector functions, Protein Cell, 2018, pp. 63-73, vol. 9 No. 1.

(Continued)

Primary Examiner — Robert B Mondesi
Assistant Examiner — Mohammad Y Meah
(74) Attorney, Agent, or Firm — Bayramoglu Law Offices LLC

(57) ABSTRACT

Provided are a mutant of an immunoglobulin degrading enzyme IdeE, a protein comprising the mutant, and a use of a composition and a kit in preparation of a drug for reducing the level of IgG in a subject. The mutant has amino acid substitution, N-terminal truncated and/or C-terminal truncated on one or more of positions 8, 10, 24, 59, 97, and 280 of the amino acid sequence shown in SEQ ID NO: 2, and the mutant has the function of the immunoglobulin degrading enzyme IdeE, and has higher activity and thermal stability than wild-type IdeE.

14 Claims, 17 Drawing Sheets
Specification includes a Sequence Listing.

(56) References Cited

OTHER PUBLICATIONS

Jonathan T. Sockolosky, et al., The neonatal Fc receptor, FcRn, as a target for drug delivery and therapy, Advanced Drug Delivery Reviews, 2014, pp. 1-16.

Joshua D. Freedman, et al., An Oncolytic Virus Expressing a T-cell Engager Simultaneously Targets Cancer and Immunosuppressive Stromal Cells, Cancer Res, 2018, pp. 6852-686, vol. 78 No. 24.

Mark A. Batzer, et al., Enhanced evolutionary PCR using oligonucleotides with inosine at the 3'-terminus, Nucleic Acids Research, 1991, p. 5081, vol. 19 No. 18.

Eiko Ohtsuk, et al., An Alternative Approach to Deoxyoligonucleotides as Hybridization Probes by Insertion of Deoxyinosine at Ambiguous Codon Positions, The Journal of Biological Chemistry, 1985, pp. 2605-2608, vol. 260 No. 5.

Gian Maria Rossolini, et al., Use of deoxyinosine-containing primers vs degenerate primers for polymerase chain reaction based on ambiguous sequence information, Molecular and Cellular Probes, 1994, pp. 91-98, vol. 8.

\* cited by examiner

1: non-digested IgG  2: T8D;  3: T8W;  4: T24A;  5: A59L;
6: A59V;  7: E97D;  8: R280H;  9: IdeE 1: T8D;  2: T8W;  3: T24A;  4: A59L;  5: A59V;
6: E97D;  7: R280H;  8: IdeE 1: WT_del15; 2: WT_del16; 3: WT_del17;
4: WT_del18; 5: WT_del19; 6: IdeE 1: WT_del15; 2: WT_del16; 3: WT_del17;
4: WT_del18; 5: WT_del19; 6: IdeE 1: WT_delC10; 2: WT_delC5; 3: IdeE 1: T24A_del18; 2: A59L_del18; 3: A59V_del18;
4: E97D_del18; 5: R280H_del18

1: T24A_del18; 2: A59L_del18; 3: A59V_del18;
4: E97D_del18; 5: R280H_del18

1: 2U/µl IdeS; 2: 1U/µl IdeS; 3: 0.5U/µl IdeS; 4: 0.25U/µl IdeS; 5: 0.125U/µl IdeS; 6: non-digested IgG1; 7: 20µg/mL E97D_del18; 8: 10µg/mL E97D_del18; 9: 5µg/mL E97D_del18; 10: 2.5µg/mL E97D_del18; 11: 1.25µg/mL E97D_del18

1: 0.4U/µl IdeZ; 2: 0.2U/µl IdeZ; 3: 0.1U/µl IdeZ; 4: 0.05U/µl IdeZ; 5: 0.025U/µl IdeZ; 6: non-digested IgG1; 7: 20µg/mL E97D_del18; 8: 10µg/mL E97D_del18; 9: 5µg/mL E97D_del18; 10: 2.5µg/mL E97D_del18; 11: 1.25µg/mL E97D_del18

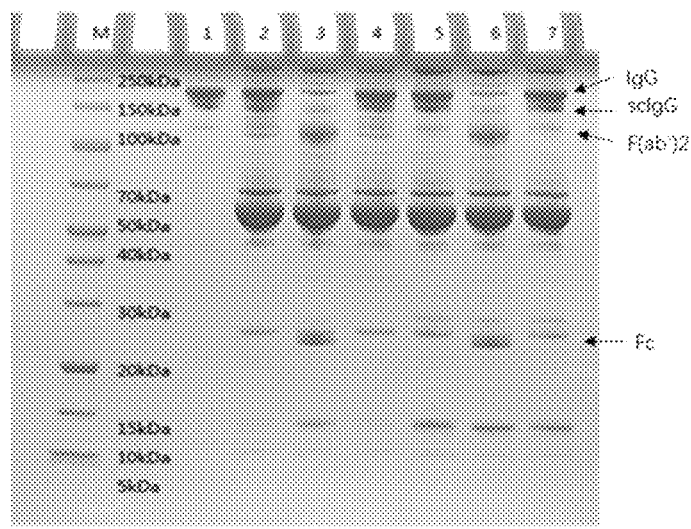

1. IVIg control;2. Mouse serum control group;3. Normal mouse serum enzymatic cleavage group;4. Iodoacetic acid-treated mouse serum group;5. Mouse plasma control group;6. Normal mouse plasma enzymatic cleavage group;7. Iodoacetic acid-treated mouse plasma group

FIG. 10

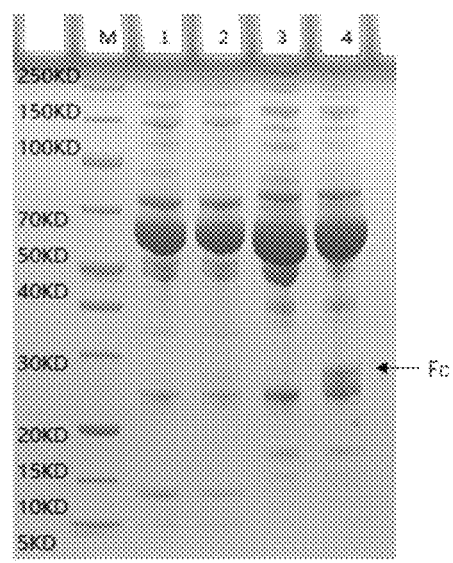

1. Mouse serum control group;2. Mouse serum enzymatic cleavage group;3. Human serum control group;4. Human serum enzymatic cleavage group

FIG. 11

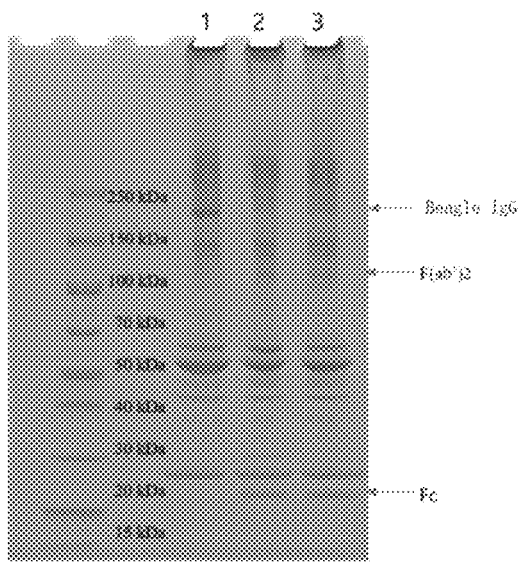

1. Beagle dog serum control group; 2. Beagle dog serum enzymatic cleavage group with concentration of E97D_del18 of 0.025 mg/ml; 3. Beagle dog serum enzymatic cleavage group with concentration of E97D_del18 of 1 mg/ml

FIG. 12A

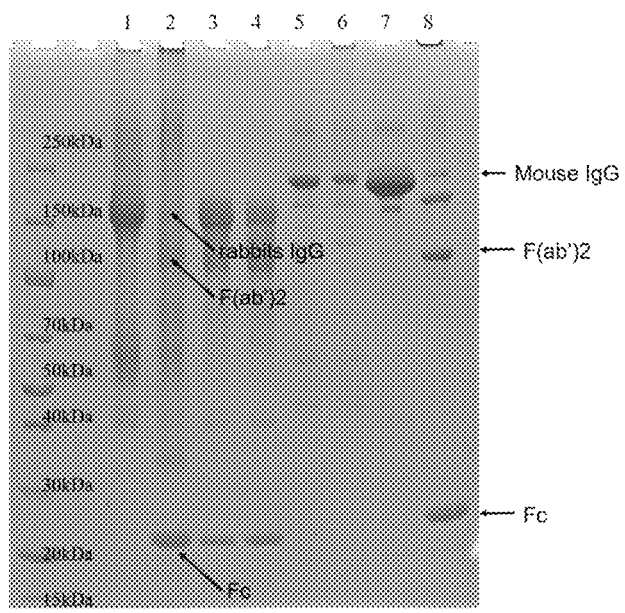

1. anti-PH20 rabbit polyclonal antibody IgG control group; 2. anti-PH20 rabbit polyclonal antibody IgG enzymatic cleavage group; 3. anti-IdeE rabbit polyclonal antibody IgG control group; 4. anti-IdeE rabbit polyclonal antibody IgG enzymatic cleavage group; 5. anti-FSH structure antibody mouse monoclonal antibody IgG1 control group; 6. anti-FSH structure antibody mouse monoclonal pit body IgG1 enzymatic cleavage group; 7. anti-EPO mouse monoclonal antibody IgG2a control group; 8. anti-EPO mouse monoclonal antibody IgG2a enzymatic cleavage group

FIG. 12B

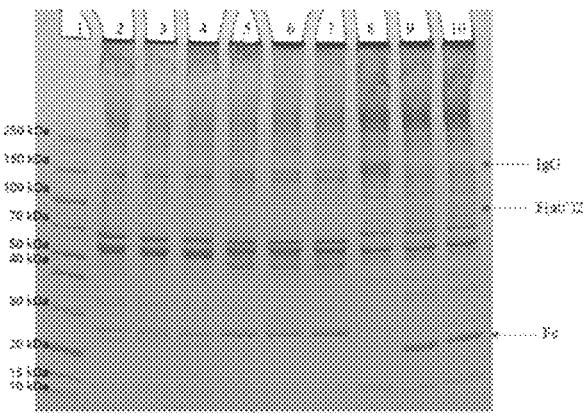

1. SD rat serum control group;2.SD rat serum enzymatic cleavage group with the concentration of E97D_del18 of 0.5 mg/ml;3.SD rat serum enzymatic cleavage group with the concentration of E97D_del18 of 0.025 mg/ml;4.ICR mouse serum control group;5.ICR mouse serum enzymatic cleavage group with concentration of E97D_del18 of 0.5 mg/ml;6.ICR mouse serum enzymatic cleavage group with concentration of E97D_del18 of 0.025 mg/ml;7.New Zealand rabbit serum control group; 8: New Zealand rabbit serum enzymatic cleavage group with the concentration of E97D_del18 of 0.5 mg/ml;9:New Zealand rabbit serum enzymatic cleavage group with the concentration of E97D_del18 of 0.025 mg/ml

FIG. 12C

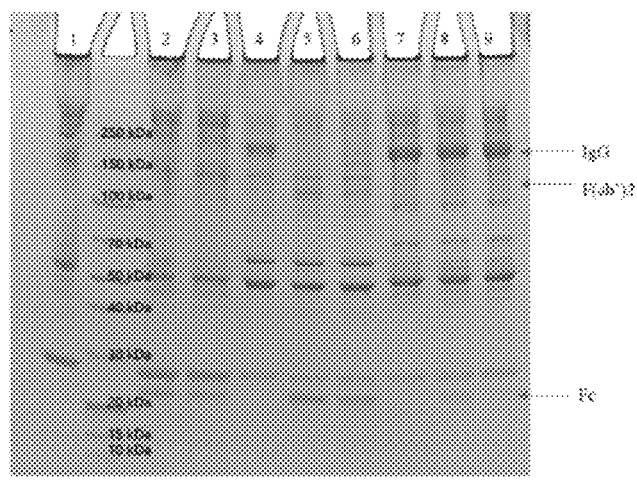

1.Beagle dog serum control group;2.Beagle dog serum enzymatic cleavage group with concentration of E97D_del18 of 0.5 mg/ml;3.Beagle dog serum enzymatic cleavage group with concentration of E97D_del18 of 0.025 mg/ml;4.Cynomolgus monkey serum control group;5.Cynomolgus monkey serum enzymatic cleavage group with concentration of E97D_del18 of 0.5 mg/ml;6.Cynomolgus monkey enzymatic cleavage group with concentration of E97D_del18 of 0.025 mg/ml;7.Bama miniature pig serum control group; 8: Bama miniature pig serum enzymatic cleavage group with concentration of E97D_del18 of 0.5 mg/ml;9:Bama miniature pig enzymatic cleavage group with concentration of E97D_del18 of 0.025 mg/ml

FIG. 12D

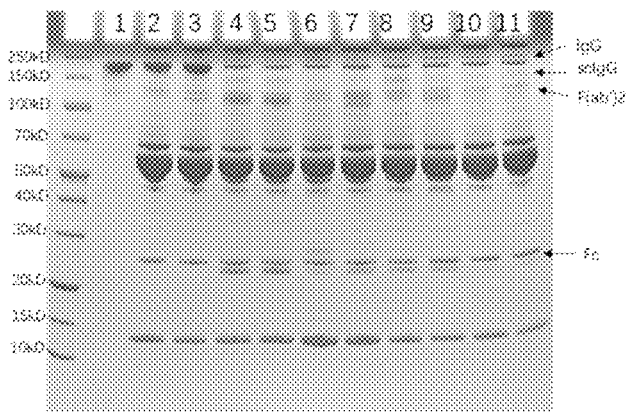

1. IVIg control; 2. Serum before injection with E97D_del18 of mouse; 3. Serum before injection with E97D_del18 of mouse 2; 4. Serum 15 min after injection with E97D_del18 of mouse 1; 5. Serum 15 min after injection with E97D_del18 of mouse 2; 6. Serum 2 h after injection with E97D_del18 of mouse 1; 7. Serum 2 h after injection with E97D_del18 of mouse 2; 8: Serum 6 h after injection with E97D_del18 of mouse 1; 9: Serum 6 h after injection with E97D_del18 of mouse 2; 10. Serum 24 h after injection with E97D_del18 of mouse 1; 11. Serum 24 h after injection with E97D_del18 of mouse 2

FIG. 13

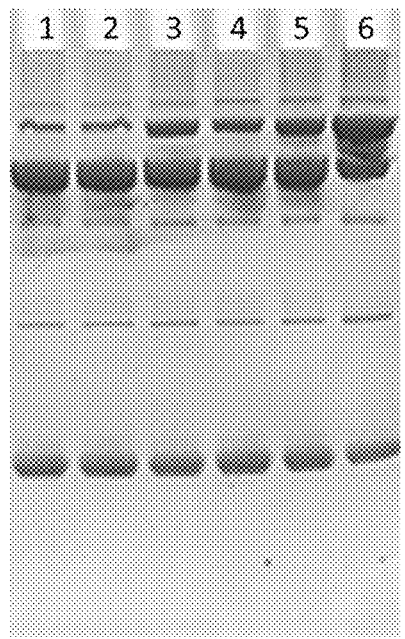

1: E97D_del18_delC5; 2: E97D_del18_delC10;
3: A59V_del18_delC5; 4: A59L_del18_delC5;
5: R280H_del18_delC5; 6: IdeE

FIG. 14A

SEQUENCE LISTING

```
Sequence total quantity: 36
SEQ ID NO: 1            moltype = AA  length = 349
FEATURE                 Location/Qualifiers
REGION                  1..349
                        note = IdeE full sequence
source                  1..349
                        mol_type = protein
                        organism = synthetic construct
SEQUENCE: 1
MKTIAYPNKP HSLSAGLLTA IAIFSLASSN ITYADDYQRN ATEAYAKEVP HQITSVWTKG   60
VTPLTPEQFR YNNEDVIHAP YLAHQGWYDI TKAFDGKDNL LCGAATAGNM LHWWFDQNKT  120
EIEAYLSKHP EKQKIIFNNQ ELFDLKAAID TKDSQTNSQL FNYFRDKAFP NLSARQLGVM  180
PDLVLDMFIN GYYLNVFKTQ STDVNRPYQD KDKRGGIFDA VFTRGDQTTL LTARHDLKNK  240
GLNDISTIIK QELTEGRALA LSHTYANVSI SHVINLWGAD FNAEGNLEAI YVTDSDANAS  300
IGMKKYFVGI NAHRHVAISA KKIEGENIGA QVLGLFTLSS GKDIWQKLS              349

SEQ ID NO: 2            moltype = AA  length = 315
FEATURE                 Location/Qualifiers
REGION                  1..315
                        note = IdeE sequence
source                  1..315
                        mol_type = protein
                        organism = synthetic construct
SEQUENCE: 2
DDYQRNATEA YAKEVPHQIT SVWTKGVTPL TPEQFRYNNE DVIHAPYLAH QGWYDITKAF   60
DGKDNLLCGA ATAGNMLHWW FDQNKTEIEA YLSKHPEKQK IIFNNQELFD LKAAIDTKDS  120
QTNSQLFNYF RDKAFPNLSA RQLGVMPDLV LDMFINGYYL NVFKTQSTDV NRPYQDKDKR  180
GGIFDAVFTR GDQTTLLTAR HDLKNKGLND ISTIIKQELT EGRALALSHT YANVSISHVI  240
NLWGADFNAE GNLEAIYVTD SDANASIGMK KYFVGINAHR HVAISAKKIE GENIGAQVLG  300
LFTLSSGKDI WQKLS                                                  315

SEQ ID NO: 3            moltype = AA  length = 315
FEATURE                 Location/Qualifiers
REGION                  1..315
                        note = T8D
source                  1..315
                        mol_type = protein
                        organism = synthetic construct
SEQUENCE: 3
DDYQRNADEA YAKEVPHQIT SVWTKGVTPL TPEQFRYNNE DVIHAPYLAH QGWYDITKAF   60
DGKDNLLCGA ATAGNMLHWW FDQNKTEIEA YLSKHPEKQK IIFNNQELFD LKAAIDTKDS  120
QTNSQLFNYF RDKAFPNLSA RQLGVMPDLV LDMFINGYYL NVFKTQSTDV NRPYQDKDKR  180
GGIFDAVFTR GDQTTLLTAR HDLKNKGLND ISTIIKQELT EGRALALSHT YANVSISHVI  240
```

```
NLWGADFNAE GNLEAIYVTD SDANASIGMK KYFVGINAHR HVAISAKKIE GENIGAQVLG    300
LFTLSSGKDI WQKLS                                                    315

SEQ ID NO: 4              moltype = AA  length = 315
FEATURE                   Location/Qualifiers
REGION                    1..315
                          note = T8E
source                    1..315
                          mol_type = protein
                          organism = synthetic construct
SEQUENCE: 4
DDYQRNAEEA YAKEVPHQIT SVWTKGVTPL TPEQFRYNNE DVIHAPYLAH QGWYDITKAF    60
DGKDNLLCGA ATAGNMLHWW FDQNKTEIEA YLSKHPEKQK IIFNNQELFD LKAAIDTKDS    120
QTNSQLFNYF RDKAFPNLSA RQLGVMPDLV LDMFINGYYL NVFKTQSTDV NRPYQDKDKR    180
GGIFDAVFTR GDQTTLLTAR HDLKNKGLND ISTIIKQELT EGRALALSHT YANVSISHVI    240
NLWGADFNAE GNLEAIYVTD SDANASIGMK KYFVGINAHR HVAISAKKIE GENIGAQVLG    300
LFTLSSGKDI WQKLS                                                    315

SEQ ID NO: 5              moltype = AA  length = 315
FEATURE                   Location/Qualifiers
REGION                    1..315
                          note = T8W
source                    1..315
                          mol_type = protein
                          organism = synthetic construct
SEQUENCE: 5
DDYQRNAWEA YAKEVPHQIT SVWTKGVTPL TPEQFRYNNE DVIHAPYLAH QGWYDITKAF    60
DGKDNLLCGA ATAGNMLHWW FDQNKTEIEA YLSKHPEKQK IIFNNQELFD LKAAIDTKDS    120
QTNSQLFNYF RDKAFPNLSA RQLGVMPDLV LDMFINGYYL NVFKTQSTDV NRPYQDKDKR    180
GGIFDAVFTR GDQTTLLTAR HDLKNKGLND ISTIIKQELT EGRALALSHT YANVSISHVI    240
NLWGADFNAE GNLEAIYVTD SDANASIGMK KYFVGINAHR HVAISAKKIE GENIGAQVLG    300
LFTLSSGKDI WQKLS                                                    315

SEQ ID NO: 6              moltype = AA  length = 315
FEATURE                   Location/Qualifiers
REGION                    1..315
                          note = T8Y
source                    1..315
                          mol_type = protein
                          organism = synthetic construct
SEQUENCE: 6
DDYQRNAYEA YAKEVPHQIT SVWTKGVTPL TPEQFRYNNE DVIHAPYLAH QGWYDITKAF    60
DGKDNLLCGA ATAGNMLHWW FDQNKTEIEA YLSKHPEKQK IIFNNQELFD LKAAIDTKDS    120
QTNSQLFNYF RDKAFPNLSA RQLGVMPDLV LDMFINGYYL NVFKTQSTDV NRPYQDKDKR    180
GGIFDAVFTR GDQTTLLTAR HDLKNKGLND ISTIIKQELT EGRALALSHT YANVSISHVI    240
NLWGADFNAE GNLEAIYVTD SDANASIGMK KYFVGINAHR HVAISAKKIE GENIGAQVLG    300
LFTLSSGKDI WQKLS                                                    315

SEQ ID NO: 7              moltype = AA  length = 315
FEATURE                   Location/Qualifiers
REGION                    1..315
                          note = A10K
source                    1..315
                          mol_type = protein
                          organism = synthetic construct
SEQUENCE: 7
DDYQRNATEK YAKEVPHQIT SVWTKGVTPL TPEQFRYNNE DVIHAPYLAH QGWYDITKAF    60
DGKDNLLCGA ATAGNMLHWW FDQNKTEIEA YLSKHPEKQK IIFNNQELFD LKAAIDTKDS    120
QTNSQLFNYF RDKAFPNLSA RQLGVMPDLV LDMFINGYYL NVFKTQSTDV NRPYQDKDKR    180
GGIFDAVFTR GDQTTLLTAR HDLKNKGLND ISTIIKQELT EGRALALSHT YANVSISHVI    240
NLWGADFNAE GNLEAIYVTD SDANASIGMK KYFVGINAHR HVAISAKKIE GENIGAQVLG    300
LFTLSSGKDI WQKLS                                                    315

SEQ ID NO: 8              moltype = AA  length = 315
FEATURE                   Location/Qualifiers
REGION                    1..315
                          note = A10R
source                    1..315
                          mol_type = protein
                          organism = synthetic construct
SEQUENCE: 8
DDYQRNATER YAKEVPHQIT SVWTKGVTPL TPEQFRYNNE DVIHAPYLAH QGWYDITKAF    60
DGKDNLLCGA ATAGNMLHWW FDQNKTEIEA YLSKHPEKQK IIFNNQELFD LKAAIDTKDS    120
QTNSQLFNYF RDKAFPNLSA RQLGVMPDLV LDMFINGYYL NVFKTQSTDV NRPYQDKDKR    180
GGIFDAVFTR GDQTTLLTAR HDLKNKGLND ISTIIKQELT EGRALALSHT YANVSISHVI    240
NLWGADFNAE GNLEAIYVTD SDANASIGMK KYFVGINAHR HVAISAKKIE GENIGAQVLG    300
LFTLSSGKDI WQKLS                                                    315

SEQ ID NO: 9              moltype = AA  length = 315
```

```
FEATURE              Location/Qualifiers
REGION               1..315
                     note = T24A
source               1..315
                     mol_type = protein
                     organism = synthetic construct
SEQUENCE: 9
DDYQRNATEA YAKEVPHQIT SVWAKGVTPL TPEQFRYNNE DVIHAPYLAH QGWYDITKAF    60
DGKDNLLCGA ATAGNMLHWW FDQNKTEIEA YLSKHPEKQK IIFNNQELFD LKAAIDTKDS   120
QTNSQLFNYF RDKAFPNLSA RQLGVMPDLV LDMFINGYYL NVFKTQSTDV NRPYQDKDKR   180
GGIFDAVFTR GDQTTLLTAR HDLKNKGLND ISTIIKQELT EGRALALSHT YANVSISHVI   240
NLWGADFNAE GNLEAIYVTD SDANASIGMK KYFVGINAHR HVAISAKKIE GENIGAQVLG   300
LFTLSSGKDI WQKLS                                                   315

SEQ ID NO: 10         moltype = AA  length = 315
FEATURE              Location/Qualifiers
REGION               1..315
                     note = T24G
source               1..315
                     mol_type = protein
                     organism = synthetic construct
SEQUENCE: 10
DDYQRNATEA YAKEVPHQIT SVWGKGVTPL TPEQFRYNNE DVIHAPYLAH QGWYDITKAF    60
DGKDNLLCGA ATAGNMLHWW FDQNKTEIEA YLSKHPEKQK IIFNNQELFD LKAAIDTKDS   120
QTNSQLFNYF RDKAFPNLSA RQLGVMPDLV LDMFINGYYL NVFKTQSTDV NRPYQDKDKR   180
GGIFDAVFTR GDQTTLLTAR HDLKNKGLND ISTIIKQELT EGRALALSHT YANVSISHVI   240
NLWGADFNAE GNLEAIYVTD SDANASIGMK KYFVGINAHR HVAISAKKIE GENIGAQVLG   300
LFTLSSGKDI WQKLS                                                   315

SEQ ID NO: 11         moltype = AA  length = 315
FEATURE              Location/Qualifiers
REGION               1..315
                     note = T24S
source               1..315
                     mol_type = protein
                     organism = synthetic construct
SEQUENCE: 11
DDYQRNATEA YAKEVPHQIT SVWSKGVTPL TPEQFRYNNE DVIHAPYLAH QGWYDITKAF    60
DGKDNLLCGA ATAGNMLHWW FDQNKTEIEA YLSKHPEKQK IIFNNQELFD LKAAIDTKDS   120
QTNSQLFNYF RDKAFPNLSA RQLGVMPDLV LDMFINGYYL NVFKTQSTDV NRPYQDKDKR   180
GGIFDAVFTR GDQTTLLTAR HDLKNKGLND ISTIIKQELT EGRALALSHT YANVSISHVI   240
NLWGADFNAE GNLEAIYVTD SDANASIGMK KYFVGINAHR HVAISAKKIE GENIGAQVLG   300
LFTLSSGKDI WQKLS                                                   315

SEQ ID NO: 12         moltype = AA  length = 315
FEATURE              Location/Qualifiers
REGION               1..315
                     note = A59I
source               1..315
                     mol_type = protein
                     organism = synthetic construct
SEQUENCE: 12
DDYQRNATEA YAKEVPHQIT SVWTKGVTPL TPEQFRYNNE DVIHAPYLAH QGWYDITKIF    60
DGKDNLLCGA ATAGNMLHWW FDQNKTEIEA YLSKHPEKQK IIFNNQELFD LKAAIDTKDS   120
QTNSQLFNYF RDKAFPNLSA RQLGVMPDLV LDMFINGYYL NVFKTQSTDV NRPYQDKDKR   180
GGIFDAVFTR GDQTTLLTAR HDLKNKGLND ISTIIKQELT EGRALALSHT YANVSISHVI   240
NLWGADFNAE GNLEAIYVTD SDANASIGMK KYFVGINAHR HVAISAKKIE GENIGAQVLG   300
LFTLSSGKDI WQKLS                                                   315

SEQ ID NO: 13         moltype = AA  length = 315
FEATURE              Location/Qualifiers
REGION               1..315
                     note = A59L
source               1..315
                     mol_type = protein
                     organism = synthetic construct
SEQUENCE: 13
DDYQRNATEA YAKEVPHQIT SVWTKGVTPL TPEQFRYNNE DVIHAPYLAH QGWYDITKLF    60
DGKDNLLCGA ATAGNMLHWW FDQNKTEIEA YLSKHPEKQK IIFNNQELFD LKAAIDTKDS   120
QTNSQLFNYF RDKAFPNLSA RQLGVMPDLV LDMFINGYYL NVFKTQSTDV NRPYQDKDKR   180
GGIFDAVFTR GDQTTLLTAR HDLKNKGLND ISTIIKQELT EGRALALSHT YANVSISHVI   240
NLWGADFNAE GNLEAIYVTD SDANASIGMK KYFVGINAHR HVAISAKKIE GENIGAQVLG   300
LFTLSSGKDI WQKLS                                                   315

SEQ ID NO: 14         moltype = AA  length = 315
FEATURE              Location/Qualifiers
REGION               1..315
                     note = A59V
source               1..315
```

```
                                 mol_type = protein
                                 organism = synthetic construct
SEQUENCE: 14
DDYQRNATEA YAKEVPHQIT SVWTKGVTPL TPEQFRYNNE DVIHAPYLAH QGWYDITKVF    60
DGKDNLLCGA ATAGNMLHWW FDQNKTEIEA YLSKHPEKQK IIFNNQELDN LKAAIDTKDS   120
QTNSQLFNYF RDKAFPNLSA RQLGVMPDLV LDMFINGYYL NVFKTQSTDV NRPYQDKDKR   180
GGIFDAVFTR GDQTTLLTAR HDLKNKGLND ISTIIKQELT EGRALALSHT YANVSISHVI   240
NLWGADFNAE GNLEAIYVTD SDANASIGMK KYFVGINAHR HVAISAKKIE GENIGAQVLG   300
LFTLSSGKDI WQKLS                                                   315

SEQ ID NO: 15           moltype = AA  length = 315
FEATURE                 Location/Qualifiers
REGION                  1..315
                        note = E97D
source                  1..315
                        mol_type = protein
                        organism = synthetic construct
SEQUENCE: 15
DDYQRNATEA YAKEVPHQIT SVWTKGVTPL TPEQFRYNNE DVIHAPYLAH QGWYDITKAF    60
DGKDNLLCGA ATAGNMLHWW FDQNKTEIEA YLSKHPDKQK IIFNNQELFD LKAAIDTKDS   120
QTNSQLFNYF RDKAFPNLSA RQLGVMPDLV LDMFINGYYL NVFKTQSTDV NRPYQDKDKR   180
GGIFDAVFTR GDQTTLLTAR HDLKNKGLND ISTIIKQELT EGRALALSHT YANVSISHVI   240
NLWGADFNAE GNLEAIYVTD SDANASIGMK KYFVGINAHR HVAISAKKIE GENIGAQVLG   300
LFTLSSGKDI WQKLS                                                   315

SEQ ID NO: 16           moltype = AA  length = 315
FEATURE                 Location/Qualifiers
REGION                  1..315
                        note = R280H
source                  1..315
                        mol_type = protein
                        organism = synthetic construct
SEQUENCE: 16
DDYQRNATEA YAKEVPHQIT SVWTKGVTPL TPEQFRYNNE DVIHAPYLAH QGWYDITKAF    60
DGKDNLLCGA ATAGNMLHWW FDQNKTEIEA YLSKHPEKQK IIFNNQELFD LKAAIDTKDS   120
QTNSQLFNYF RDKAFPNLSA RQLGVMPDLV LDMFINGYYL NVFKTQSTDV NRPYQDKDKR   180
GGIFDAVFTR GDQTTLLTAR HDLKNKGLND ISTIIKQELT EGRALALSHT YANVSISHVI   240
NLWGADFNAE GNLEAIYVTD SDANASIGMK KYFVGINAHH HVAISAKKIE GENIGAQVLG   300
LFTLSSGKDI WQKLS                                                   315

SEQ ID NO: 17           moltype = AA  length = 315
FEATURE                 Location/Qualifiers
REGION                  1..315
                        note = R280K
source                  1..315
                        mol_type = protein
                        organism = synthetic construct
SEQUENCE: 17
DDYQRNATEA YAKEVPHQIT SVWTKGVTPL TPEQFRYNNE DVIHAPYLAH QGWYDITKAF    60
DGKDNLLCGA ATAGNMLHWW FDQNKTEIEA YLSKHPEKQK IIFNNQELFD LKAAIDTKDS   120
QTNSQLFNYF RDKAFPNLSA RQLGVMPDLV LDMFINGYYL NVFKTQSTDV NRPYQDKDKR   180
GGIFDAVFTR GDQTTLLTAR HDLKNKGLND ISTIIKQELT EGRALALSHT YANVSISHVI   240
NLWGADFNAE GNLEAIYVTD SDANASIGMK KYFVGINAHK HVAISAKKIE GENIGAQVLG   300
LFTLSSGKDI WQKLS                                                   315

SEQ ID NO: 18           moltype = AA  length = 300
FEATURE                 Location/Qualifiers
REGION                  1..300
                        note = WT_del15
source                  1..300
                        mol_type = protein
                        organism = synthetic construct
SEQUENCE: 18
PHQITSVWTK GVTPLTPEQF RYNNEDVIHA PYLAHQGWYD ITKAFDGKDN LLCGAATAGN    60
MLHWWFDQNK TEIEAYLSKH PEKQKIIFNN QELFDLKAAI DTKDSQTNSQ LFNYFRDKAF   120
PNLSARQLGV MPDLVLDMFI NGYYLNVFKT QSTDVNRPYQ DKDKRGGIFD AVFTRGDQTT   180
LLTARHDLKN KGLNDISTII KQELTEGRAL ALSHTYANVS ISHVINLWGA DFNAEGNLEA   240
IYVTDSDANA SIGMKKYFVG INAHRHVAIS AKKIEGENIG AQVLGLFTLS SGKDIWQKLS   300

SEQ ID NO: 19           moltype = AA  length = 299
FEATURE                 Location/Qualifiers
REGION                  1..299
                        note = WT_del16
source                  1..299
                        mol_type = protein
                        organism = synthetic construct
SEQUENCE: 19
HQITSVWTKG VTPLTPEQFR YNNEDVIHAP YLAHQGWYDI TKAFDGKDNL LCGAATAGNM    60
LHWWFDQNKT EIEAYLSKHP EKQKIIFNNQ ELFDLKAAID TKDSQTNSQL FNYFRDKAFP   120
```

```
NLSARQLGVM PDLVLDMFIN GYYLNVFKTQ STDVNRPYQD KDKRGGIFDA VFTRGDQTTL    180
LTARHDLKNK GLNDISTIIK QELTEGRALA LSHTYANVSI SHVINLWGAD FNAEGNLEAI    240
YVTDSDANAS IGMKKYFVGI NAHRHVAISA KKIEGENIGA QVLGLFTLSS GKDIWQKLS     299

SEQ ID NO: 20            moltype = AA   length = 298
FEATURE                  Location/Qualifiers
REGION                   1..298
                         note = WT_del17
source                   1..298
                         mol_type = protein
                         organism = synthetic construct
SEQUENCE: 20
QITSVWTKGV TPLTPEQFRY NNEDVIHAPY LAHQGWYDIT KAFDGKDNLL CGAATAGNML    60
HWWFDQNKTE IEAYLSKHPE KQKIIFNNQE LFDLKAAIDT KDSQTNSQLF NYFRDKAFPN    120
LSARQLGVMP DLVLDMFING YYLNVFKTQS TDVNRPYQDK DKRGGIFDAV FTRGDQTTLL    180
TARHDLKNKG LNDISTIIKQ ELTEGRALAL SHTYANVSIS HVINLWGADF NAEGNLEAIY    240
VTDSDANASI GMKKYFVGIN AHRHVAISAK KIEGENIGAQ VLGLFTLSSG KDIWQKLS      298

SEQ ID NO: 21            moltype = AA   length = 297
FEATURE                  Location/Qualifiers
REGION                   1..297
                         note = WT_del18
source                   1..297
                         mol_type = protein
                         organism = synthetic construct
SEQUENCE: 21
ITSVWTKGVT PLTPEQFRYN NEDVIHAPYL AHQGWYDITK AFDGKDNLLC GAATAGNMLH    60
WWFDQNKTEI EAYLSKHPEK QKIIFNNQEL FDLKAAIDTK DSQTNSQLFN YFRDKAFPNL    120
SARQLGVMPD LVLDMFINGY YLNVFKTQST DVNRPYQDKD KRGGIFDAVF TRGDQTTLLT    180
ARHDLKNKGL NDISTIIKQE LTEGRALALS HTYANVSISH VINLWGADFN AEGNLEAIYV    240
TDSDANASIG MKKYFVGINA HRHVAISAKK IEGENIGAQV LGLFTLSSGK DIWQKLS       297

SEQ ID NO: 22            moltype = AA   length = 296
FEATURE                  Location/Qualifiers
REGION                   1..296
                         note = WT_del19
source                   1..296
                         mol_type = protein
                         organism = synthetic construct
SEQUENCE: 22
TSVWTKGVTP LTPEQFRYNN EDVIHAPYLA HQGWYDITKA FDGKDNLLCG AATAGNMLHW    60
WFDQNKTEIE AYLSKHPEKQ KIIFNNQELF DLKAAIDTKD SQTNSQLFNY FRDKAFPNLS    120
ARQLGVMPDL VLDMFINGYY LNVFKTQSTD VNRPYQDKDK RGGIFDAVFT RGDQTTLLTA    180
RHDLKNKGLN DISTIIKQEL TEGRALALSH TYANVSISHV INLWGADFNA EGNLEAIYVT    240
DSDANASIGM KKYFVGINAH RHVAISAKKI EGENIGAQVL GLFTLSSGKD IWQKLS        296

SEQ ID NO: 23            moltype = AA   length = 310
FEATURE                  Location/Qualifiers
REGION                   1..310
                         note = WT_delC5
source                   1..310
                         mol_type = protein
                         organism = synthetic construct
SEQUENCE: 23
DDYQRNATEA YAKEVPHQIT SVWTKGVTPL TPEQFRYNNE DVIHAPYLAH QGWYDITKAF    60
DGKDNLLCGA ATAGNMLHWW FDQNKTEIEA YLSKHPEKQK IIFNNQELFD LKAAIDTKDS    120
QTNSQLFNYF RDKAFPNLSA RQLGVMPDLV LDMFINGYYL NVFKTQSTDV NRPYQDKDKR    180
GGIFDAVFTR GDQTTLLTAR HDLKNKGLND ISTIIKQELT EGRALALSHT YANVSISHVI    240
NLWGADFNAE GNLEAIYVTD SDANASIGMK KYFVGINAHR HVAISAKKIE GENIGAQVLG    300
LFTLSSGKDI                                                          310

SEQ ID NO: 24            moltype = AA   length = 305
FEATURE                  Location/Qualifiers
REGION                   1..305
                         note = WT_delC10
source                   1..305
                         mol_type = protein
                         organism = synthetic construct
SEQUENCE: 24
DDYQRNATEA YAKEVPHQIT SVWTKGVTPL TPEQFRYNNE DVIHAPYLAH QGWYDITKAF    60
DGKDNLLCGA ATAGNMLHWW FDQNKTEIEA YLSKHPEKQK IIFNNQELFD LKAAIDTKDS    120
QTNSQLFNYF RDKAFPNLSA RQLGVMPDLV LDMFINGYYL NVFKTQSTDV NRPYQDKDKR    180
GGIFDAVFTR GDQTTLLTAR HDLKNKGLND ISTIIKQELT EGRALALSHT YANVSISHVI    240
NLWGADFNAE GNLEAIYVTD SDANASIGMK KYFVGINAHR HVAISAKKIE GENIGAQVLG    300
LFTLS                                                               305

SEQ ID NO: 25            moltype = AA   length = 297
FEATURE                  Location/Qualifiers
REGION                   1..297
```

```
                        note        = T24A_del18
source                  1..297
                        mol_type    = protein
                        organism    = synthetic construct
SEQUENCE: 25
ITSVWAKGVT PLTPEQFRYN NEDVIHAPYL AHQGWYDITK AFDGKDNLLC GAATAGNMLH    60
WWFDQNKTEI EAYLSKHPEK QKIIFNNQEL FDLKAAIDTK DSQTNSQLFN YFRDKAFPNL   120
SARQLGVMPD LVLDMFINGY YLNVFKTQST DVNRPYQDKD KRGGIFDAVF TRGDQTTLLT   180
ARHDLKNKGL NDISTIIKQE LTEGRALALS HTYANVSISH VINLWGADFN AEGNLEAIYV   240
TDSDANASIG MKKYFVGINA HRHVAISAKK IEGENIGAQV LGLFTLSSGK DIWQKLS      297

SEQ ID NO: 26           moltype = AA   length = 297
FEATURE                 Location/Qualifiers
REGION                  1..297
                        note        = A59L_del18
source                  1..297
                        mol_type    = protein
                        organism    = synthetic construct
SEQUENCE: 26
ITSVWTKGVT PLTPEQFRYN NEDVIHAPYL AHQGWYDITK LFDGKDNLLC GAATAGNMLH    60
WWFDQNKTEI EAYLSKHPEK QKIIFNNQEL FDLKAAIDTK DSQTNSQLFN YFRDKAFPNL   120
SARQLGVMPD LVLDMFINGY YLNVFKTQST DVNRPYQDKD KRGGIFDAVF TRGDQTTLLT   180
ARHDLKNKGL NDISTIIKQE LTEGRALALS HTYANVSISH VINLWGADFN AEGNLEAIYV   240
TDSDANASIG MKKYFVGINA HRHVAISAKK IEGENIGAQV LGLFTLSSGK DIWQKLS      297

SEQ ID NO: 27           moltype = AA   length = 297
FEATURE                 Location/Qualifiers
REGION                  1..297
                        note        = A59V_del18
source                  1..297
                        mol_type    = protein
                        organism    = synthetic construct
SEQUENCE: 27
ITSVWTKGVT PLTPEQFRYN NEDVIHAPYL AHQGWYDITK VFDGKDNLLC GAATAGNMLH    60
WWFDQNKTEI EAYLSKHPEK QKIIFNNQEL FDLKAAIDTK DSQTNSQLFN YFRDKAFPNL   120
SARQLGVMPD LVLDMFINGY YLNVFKTQST DVNRPYQDKD KRGGIFDAVF TRGDQTTLLT   180
ARHDLKNKGL NDISTIIKQE LTEGRALALS HTYANVSISH VINLWGADFN AEGNLEAIYV   240
TDSDANASIG MKKYFVGINA HRHVAISAKK IEGENIGAQV LGLFTLSSGK DIWQKLS      297

SEQ ID NO: 28           moltype = AA   length = 297
FEATURE                 Location/Qualifiers
REGION                  1..297
                        note        = E97D_del18
source                  1..297
                        mol_type    = protein
                        organism    = synthetic construct
SEQUENCE: 28
ITSVWTKGVT PLTPEQFRYN NEDVIHAPYL AHQGWYDITK AFDGKDNLLC GAATAGNMLH    60
WWFDQNKTEI EAYLSKHPDK QKIIFNNQEL FDLKAAIDTK DSQTNSQLFN YFRDKAFPNL   120
SARQLGVMPD LVLDMFINGY YLNVFKTQST DVNRPYQDKD KRGGIFDAVF TRGDQTTLLT   180
ARHDLKNKGL NDISTIIKQE LTEGRALALS HTYANVSISH VINLWGADFN AEGNLEAIYV   240
TDSDANASIG MKKYFVGINA HRHVAISAKK IEGENIGAQV LGLFTLSSGK DIWQKLS      297

SEQ ID NO: 29           moltype = AA   length = 297
FEATURE                 Location/Qualifiers
REGION                  1..297
                        note        = R280H_del18
source                  1..297
                        mol_type    = protein
                        organism    = synthetic construct
SEQUENCE: 29
ITSVWTKGVT PLTPEQFRYN NEDVIHAPYL AHQGWYDITK AFDGKDNLLC GAATAGNMLH    60
WWFDQNKTEI EAYLSKHPEK QKIIFNNQEL FDLKAAIDTK DSQTNSQLFN YFRDKAFPNL   120
SARQLGVMPD LVLDMFINGY YLNVFKTQST DVNRPYQDKD KRGGIFDAVF TRGDQTTLLT   180
ARHDLKNKGL NDISTIIKQE LTEGRALALS HTYANVSISH VINLWGADFN AEGNLEAIYV   240
TDSDANASIG MKKYFVGINA HHHVAISAKK IEGENIGAQV LGLFTLSSGK DIWQKLS      297

SEQ ID NO: 30           moltype = AA   length = 292
FEATURE                 Location/Qualifiers
REGION                  1..292
                        note        = E97D_del18_delC5
source                  1..292
                        mol_type    = protein
                        organism    = synthetic construct
SEQUENCE: 30
ITSVWTKGVT PLTPEQFRYN NEDVIHAPYL AHQGWYDITK AFDGKDNLLC GAATAGNMLH    60
WWFDQNKTEI EAYLSKHPDK QKIIFNNQEL FDLKAAIDTK DSQTNSQLFN YFRDKAFPNL   120
SARQLGVMPD LVLDMFINGY YLNVFKTQST DVNRPYQDKD KRGGIFDAVF TRGDQTTLLT   180
ARHDLKNKGL NDISTIIKQE LTEGRALALS HTYANVSISH VINLWGADFN AEGNLEAIYV   240
```

```
TDSDANASIG MKKYFVGINA HRHVAISAKK IEGENIGAQV LGLFTLSSGK DI            292

SEQ ID NO: 31            moltype = AA   length = 287
FEATURE                  Location/Qualifiers
REGION                   1..287
                         note = E97D_del18_delC10
source                   1..287
                         mol_type = protein
                         organism = synthetic construct
SEQUENCE: 31
ITSVWTKGVT PLTPEQFRYN NEDVIHAPYL AHQGWYDITK AFDGKDNLLC GAATAGNMLH     60
WWFDQNKTEI EAYLSKHPDK QKIIFNNQEL FDLKAAIDTK DSQTNSQLFN YFRDKAFPNL    120
SARQLGVMPD LVLDMFINGY YLNVFKTQST DVNRPYQDKD KRGGIFDAVF TRGDQTTLLT    180
ARHDLKNKGL NDISTIIKQE LTEGRALALS HTYANVSISH VINLWGADFN AEGNLEAIYV    240
TDSDANASIG MKKYFVGINA HRHVAISAKK IEGENIGAQV LGLFTLS                  287

SEQ ID NO: 32            moltype = AA   length = 292
FEATURE                  Location/Qualifiers
REGION                   1..292
                         note = A59V_del18_delC5
source                   1..292
                         mol_type = protein
                         organism = synthetic construct
SEQUENCE: 32
ITSVWTKGVT PLTPEQFRYN NEDVIHAPYL AHQGWYDITK VFDGKDNLLC GAATAGNMLH     60
WWFDQNKTEI EAYLSKHPEK QKIIFNNQEL FDLKAAIDTK DSQTNSQLFN YFRDKAFPNL    120
SARQLGVMPD LVLDMFINGY YLNVFKTQST DVNRPYQDKD KRGGIFDAVF TRGDQTTLLT    180
ARHDLKNKGL NDISTIIKQE LTEGRALALS HTYANVSISH VINLWGADFN AEGNLEAIYV    240
TDSDANASIG MKKYFVGINA HRHVAISAKK IEGENIGAQV LGLFTLSSGK DI            292

SEQ ID NO: 33            moltype = AA   length = 292
FEATURE                  Location/Qualifiers
REGION                   1..292
                         note = A59L_del18_delC5
source                   1..292
                         mol_type = protein
                         organism = synthetic construct
SEQUENCE: 33
ITSVWTKGVT PLTPEQFRYN NEDVIHAPYL AHQGWYDITK LFDGKDNLLC GAATAGNMLH     60
WWFDQNKTEI EAYLSKHPEK QKIIFNNQEL FDLKAAIDTK DSQTNSQLFN YFRDKAFPNL    120
SARQLGVMPD LVLDMFINGY YLNVFKTQST DVNRPYQDKD KRGGIFDAVF TRGDQTTLLT    180
ARHDLKNKGL NDISTIIKQE LTEGRALALS HTYANVSISH VINLWGADFN AEGNLEAIYV    240
TDSDANASIG MKKYFVGINA HRHVAISAKK IEGENIGAQV LGLFTLSSGK DI            292

SEQ ID NO: 34            moltype = AA   length = 292
FEATURE                  Location/Qualifiers
REGION                   1..292
                         note = R280H_del18_delC5
source                   1..292
                         mol_type = protein
                         organism = synthetic construct
SEQUENCE: 34
ITSVWTKGVT PLTPEQFRYN NEDVIHAPYL AHQGWYDITK AFDGKDNLLC GAATAGNMLH     60
WWFDQNKTEI EAYLSKHPEK QKIIFNNQEL FDLKAAIDTK DSQTNSQLFN YFRDKAFPNL    120
SARQLGVMPD LVLDMFINGY YLNVFKTQST DVNRPYQDKD KRGGIFDAVF TRGDQTTLLT    180
ARHDLKNKGL NDISTIIKQE LTEGRALALS HTYANVSISH VINLWGADFN AEGNLEAIYV    240
TDSDANASIG MKKYFVGINA HHHVAISAKK IEGENIGAQV LGLFTLSSGK DI            292

SEQ ID NO: 35            moltype = AA   length = 315
FEATURE                  Location/Qualifiers
REGION                   1..315
                         note = A59V/E97D/R280H
source                   1..315
                         mol_type = protein
                         organism = synthetic construct
SEQUENCE: 35
DDYQRNATEA YAKEVPHQIT SVWTKGVTPL TPEQFRYNNE DVIHAPYLAH QGWYDITKVF     60
DGKDNLLCGA ATAGNMLHWW FDQNKTEIEA YLSKHPDKII FNNQELFD LKAAIDTKDS    120
QTNSQLFNYF RDKAFPNLSA RQLGVMPDLV LDMFINGYYL NVFKTQSTDV NRPYQDKDKR    180
GGIFDAVFTR GDQTTLLTAR HDLKNKGLND ISTIIKQELT EGRALALSHT YANVSISHVI    240
NLWGADFNAE GNLEAIYVTD SDANASIGMK KYFVGINAHH HVAISAKKIE GENIGAQVLG    300
LFTLSSGKDI WQKLS                                                    315

SEQ ID NO: 36            moltype = AA   length = 297
FEATURE                  Location/Qualifiers
REGION                   1..297
                         note = KJ103
source                   1..297
                         mol_type = protein
```

```
organism = synthetic construct
SEQUENCE: 36
ITSVWTKGVT  PLTPEQFRYN  NEDVIHAPYL  AHQGWYDITK  AFDGKDNLLC  GAATAGNMLH   60
WWFDQNKTEI  EAYLSKHPDK  QKIIFNNQEL  FDLKAAIDTK  DSQTNSQLFN  YFRDKAFPNL  120
SARQLGVMPD  LVLDMFINGY  YLNVFKTQST  DVNRPYQDKD  KRGGIFDAVF  TRGDQTTLLT  180
ARHDLKNKGL  NDISTIIKQE  LTEGRALALS  HTYANVSISH  VINLWGADFN  AEGNLEAIYV  240
TDSDANASIG  MKKYFVGINA  HGHVAISAKK  IEGENIGAQV  LGLFTLSSGK  DIWQKLS     297
```

USE OF MUTANT OF IMMUNOGLOBULIN DEGRADING ENZYME IDEE

CROSS REFERENCE TO THE RELATED APPLICATIONS

This is a continuation application of International Application No. PCT/CN2022/141001, filed on Dec. 22, 2022, which is based upon and claims priority to Chinese Patent Application No. 202111577633.5, filed on Dec. 22, 2021, the entire contents of which are incorporated herein by reference.

SEQUENCE LISTING

The instant application contains a Sequence Listing which has been submitted in XML format via EFS-Web and is hereby incorporated by reference in its entirety. Said XML copy is named GBSRWA008_Sequence_Listing, created on Jun. 20, 2024, and is 56,303 bytes in size.

TECHNICAL FIELD

The present invention relates to the field of biotechnology, specifically to a mutant of an immunoglobulin degrading enzyme, a composition comprising the mutant, and a use of them in reducing the level of IgG.

BACKGROUND

*Streptococcus pyogenes* is one of the common pathogens in humans and animals, which is widely found in nature and in the oropharyngeal cavities, respiratory tracts, and intestinal tracts of humans or animals. Streptococcal infections cause related diseases, mild conditions such as suppurative dermatitis, pharyngitis, more severe diseases such as septicaemia, necrotizing fasciitis, and toxic shock syndrome. Immunoglobulin G-degrading enzyme of *Streptococcus pyogenes* (IdeS), a common A-type *Streptococcus pyogenes* (GAS) cysteine protease, has peptidyl endopeptidase activity that hydrolyzes IgG (Agniswamy J, Lei B, Musser J M et al., J Biol Chem, 2004, 279:52789-52796. Lei B, DeLeo F R, Reid S D et al., Infect Immun, 2002, 70:6880-6890. Von Pawel-Rammingen U, Johansson B P, Bjorck L. EMBO J, 2002, 21:1607-1615.). As a virulence factor of pathogenic bacteria, it can recognize the CH1 and CH2 domains of the lower hinge region of the antibody and specifically degrade IgG to obtain homogeneous F(ab)$_2$ and Fc fragments, helping GAS evade antibody-mediated phagocytosis and cytotoxicity, thereby weakening the host immune system's killing on GAS (Von Pawel-Rammingen U. J Innate Immunity, 2012, 4:132-140. Su, Y.-F. et al, Molecular Immunology, 2011, 49:134-142.).

Immunoglobulin G (IgG), as the main antibody component of serum, accounting for about 75% of serum immunoglobulin, plays a major protective role in the body's immunity and can effectively prevent infectious diseases. In addition to having a protective effect, IgG is also associated with diseases. In some autoimmune diseases, the IgG antibody reacts with a human self-molecule and IgG causes acute transplant rejection in organ transplants. IdeS specifically degrades IgG, thereby rendering IgG non-functional for immunosuppression.

At present, the IdeS for clinical use has deficiencies of poor activity and high amount of pre-existing antibodies in the human body. IdeS is a virulence factor of human pathogenic bacteria. Clinical studies have found that anti-IdeS antibodies are detected in nearly 100% of normal people under normal physiological conditions, which results in low efficiency of IdeS administration and safety problems.

Therefore, there is a need for an immunoglobulin degrading enzyme with higher safety while maintaining activity for the preparation of clinical drugs related to some diseases.

SUMMARY

A first aspect of the present invention relates to a use of a mutant of an immunoglobulin degrading enzyme IdeE comprising or consisting of the amino acid sequence shown as SEQ ID NO: 2 in the sequence listing, preferably in the preparation of a drug for the treatment of an autoantibody-mediated disorder in a subject; the mutant comprises a mutation selected from the group consisting of:
(1) substituting one or more of sites 8, 10, 24, 59, 97, and 280 of the amino acid sequence; and/or,
(2) truncating the immunoglobulin degrading enzyme IdeE to delete the first 1, first 2, first 3, first 4, first 5, first 6, first 7, first 8, first 9, first 10, first 11, first 12, first 13, first 14, first 15, first 16, first 17, first 18, or first 19 amino acid residues at the N-terminal thereof; and/or,
(3) truncating the immunoglobulin degrading enzyme IdeE to delete the last 1, last 2, last 3, last 4, last 5, last 6, last 7, last 8, last 9, or last 10 amino acid residues at the C-terminal thereof;
wherein the mutant has an activity and/or thermal stability greater than or equal to that of the immunoglobulin degrading enzyme IdeE.

The first aspect of the present invention also relates to use of a protein comprising the mutant of the present invention in the preparation of a drug for the treatment of an autoantibody-mediated disorder in a subject. Preferably the protein has a secretion signal sequence and/or methionine connected to the N-terminal of the mutant; and/or the protein has a histidine tag connected to the C-terminal of the mutant. The first aspect of the present invention also relates to the use of a composition comprising the mutant or protein of the present invention or a kit comprising a mutant or protein of the present invention in the preparation of a drug for the treatment of an autoantibody-mediated disorder in a subject, preferably the composition further comprises optionally a pharmaceutically acceptable carrier or excipient and/or an additional therapeutic agent selected from the group consisting of: (a) an antibody or an Fc-containing protein, preferably a target of the antibody is selected from the group consisting of: a cell surface protein, cytokine, hormone, enzyme, intracellular messenger, intercellular messenger, and immune checkpoint; (b) a viral vector drug, preferably the viral vector drug is selected from the group consisting of: an oncolytic virus, gene therapy virus, and viral vector vaccine; and (c) an agent capable of reducing the level of the IgG in the blood, preferably the agent capable of reducing the level of the IgG in the blood is selected from the group consisting of: an FcRn antibody, an Fc fragment variant with high affinity to FcRn.

The second aspect of the present invention relates to the use of the mutant, a protein containing the mutant, or a composition or kit containing the mutant or protein in the preparation of a drug for reducing the level of the IgG in a subject.

A third aspect of the present invention relates to the use of the mutant of the present invention, a protein comprising the mutant, or a composition or kit comprising the mutant or the protein in the preparation of a drug for the prevention and/or treatment of autoantibody-mediated organ rejection following solid organ transplantation in a subject.

A fourth aspect of the present invention relates to the use of the mutant of the present invention, a protein comprising the mutant, or a composition or kit comprising the mutant or the protein in the preparation of a drug for gene therapy, as well as to the use in the preparation of a drug for clearing neutralizing antibodies of pre-existing antiviral vectors in the body prior to viral vector-based gene therapy.

The fifth aspect of the present invention relates to the use of the mutant, the protein containing the mutant, or the composition or kit containing the mutant or protein in the preparation of a drug for treating a tumor in a subject.

A sixth aspect of the present invention relates to the use of the mutant of the present invention, a protein comprising the mutant, or a composition or kit comprising the mutant or the protein in the preparation of a drug for clearing autoantibodies in a subject such that an Fc-containing agent is more therapeutically effective.

The seventh aspect of the present invention relates to the use of the mutant, a protein containing the mutant, or a composition or kit containing the mutant or protein in the preparation of a drug for reducing the serum level of an Fc-containing agent in a subject to which the Fc-containing agent has been administered.

BRIEF DESCRIPTION OF THE DRAWINGS

FIG. 10 shows a SDS-PAGE gel electropherogram of the cleavage product resulting from digesting human IVIg by the E97D_del18 mutant in mouse serum and plasma.

FIG. 11 shows a SDS-PAGE gel electropherogram of the cleavage products of the E97D_del18 mutant in mouse and human serum.

FIGS. 12A-12D show SDS-PAGE gel electropherograms of the cleavage products resulting from digesting IgG by E97D_del18 in the serums of Beagle dog, rat, mouse, rabbit, monkey, and pig at various concentrations.

FIG. 13 shows a SDS-PAGE gel electropherogram of cleavage products resulting from digesting human IVIg by E97D_del18 at various times in mouse.

FIGS. 14A and 14B show SDS-PAGE gel electropherogram of cleavage products resulting from digesting human IgG1 by mutants with different mutation combinations and IdeE (enzyme: substrate=1:2000).

DETAILED DESCRIPTION OF THE EMBODIMENT

Figure 1:
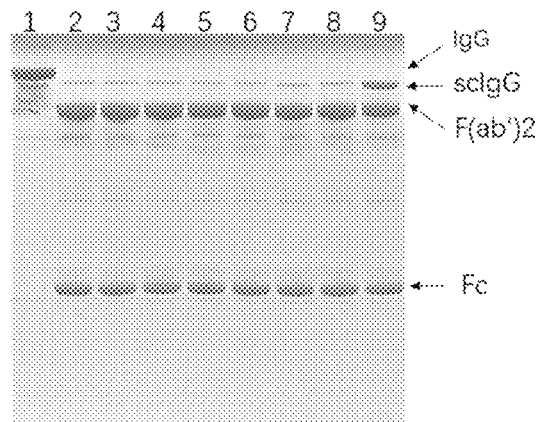
FIG. 1 shows an SDS-PAGE gel electropherogram of the cleavage products resulting from digesting human IgG1 by 7 single-point mutants and wild-type IdeE (enzyme: substrate=1:1000).

I. Mutants of Immunoglobulin Degrading Enzyme IdeE

The IdeE protease with a sequence homology of around 70% to IdeS is derived from *Streptococcus equi* ssp.equi, and is an equine pathogen (Jonas Lannergård, Bengt Guss. FEMS Microbiol Lett, 2006, 262:230-235). The two enzymes, IdeE and IdeS, digest IgG at exactly the same position, with high reproducibility, specificity and a very similar substrate range. Since IdeE is derived from equine pathogenic bacteria, it is speculated that its pre-existing antibodies in humans may be much fewer than IdeS, and is more suitable for the development of immunosuppressive agents for the treatment and prevention of diseases mediated by IgG antibodies. However, wild-type IdeE, like IdeS, also suffers from low activity.

Accordingly, the present invention relates to a mutant of the immunoglobulin degrading enzyme IdeE, the mutant having immunoglobulin degrading enzyme activity and being selected from the group consisting of:

(1) a mutant obtained by substituting one or more amino acids in positions 8, 10, 24, 59, 97, and 280 of SEQ ID NO: 2; and/or, (2) a truncated mutant at the N-terminal of SEQ ID NO: 2 selected from deleting the first 1, first 2, first 3, first 4, first 5, first 6, first 7, first 8, first 9, first 10, first 11, first 12, first 13, first 14, first 15, first 16, first 17, first 18, or first 19 amino acid sequences at the N-terminal thereof; and/or, (3) a truncated mutant at the C-terminal of SEQ ID NO: 2 selected from deleting the last 1, last 2, last 3, last 4, last 5, last 6, last 7, last 8, last 9, or last 10 amino acid sequences at the C-terminal.

The mutants of the present invention function as the immunoglobulin degrading enzyme IdeE and preferably also have improved IgG cleavage activity and thermal stability.

The term "having an activity greater than or equal to the immunoglobulin degrading enzyme IdeE" in the present invention means that the ability of the mutant to degrade immunoglobulins is better than or equal to the wild-type immunoglobulin degrading enzyme IdeE.

The term "more thermostable than IdeE" in the context of the present invention means that the mutant has a better capacity to degrade immunoglobulins than the wild-type immunoglobulin degrading enzyme IdeE under comparable conditions when maintained at a certain temperature for a certain period of time.

The mutants of the present invention are preferably produced recombinantly by genetic engineering.

Preferably, the mutant has at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the sequence shown in SEQ ID NO: 2.

More preferably, the amino acid at position 8, 10, 24, 59, 97, or 280 is substituted, e.g. the amino acid sequence of the resulting mutant is as shown in any one of SEQ ID NOS: 3-17, and SEQ ID NO: 35.

Optionally, the first 15, the first 16, the first 17, the first 18, or the first 19 amino acids of the immunoglobulin degrading enzyme IdeE at the N-terminal are deleted, and the amino acid sequence of the resulting mutant is as shown in any one of SEQ ID NOS: 18-22.

Optionally, the last 1, last 5, last 8, or last 10 amino acids of the immunoglobulin degrading enzyme IdeE at the C-terminal are deleted, for example, the amino acid sequence of the resulting mutant is as shown in any one of SEQ ID NOS: 23-24;

Optionally, the amino acid at position 8, 10, 24, 59, 97, or 280 is substituted and simultaneously the first 15, the first 16, the first 17, the first 18, or the first 19 amino acids, preferably the first 18 amino acids, of the immunoglobulin degrading enzyme IdeE at the N-terminal are deleted, e.g. the amino acid sequence of the resulting mutant is as shown in any one of SEQ ID NOS: 25-29.

Optionally, the amino acid at position 8, 10, 24, 59, 97, or 280 is substituted and simultaneously the first 15, the first 16, the first 17, the first 18, or the first 19 amino acids, preferably the first 18 amino acids, of the immunoglobulin degrading enzyme IdeE at the N-terminal are deleted, and simultaneously the last 1, last 5, last 8 or last 10 amino acids, preferably the last 5 amino acids, of the immunoglobulin degrading enzyme IdeE at the C-terminal are deleted, for example, the amino acid sequence of the resulting mutant is as shown in any one of SEQ ID NOS: 30-34.

In a preferred embodiment of the present invention, the amino acid substitution is selected from the group consisting of:

(1) substituting the threonine at position 8 of SEQ ID NO: 2 with any one of cysteine, phenylalanine, tryptophan, tyrosine, aspartic acid, glutamic acid, alanine, glycine, histidine, isoleucine, leucine, methionine, asparagine, proline, glutamine, serine, valine, arginine, and lysine;

(2) substituting the alanine at position 10 of SEQ ID NO: 2 with any one of cysteine, aspartic acid, glutamic acid, phenylalanine, glycine, histidine, isoleucine, lysine, leucine, methionine, asparagine, proline, glutamine, arginine, serine, threonine, valine, tryptophan, and tyrosine;

(3) substituting the threonine at position 24 of SEQ ID NO: 2 with any one of alanine, cysteine, aspartic acid, asparagine, glutamic acid, phenylalanine, glycine, histidine, isoleucine, lysine, leucine, methionine, proline, glutamine, arginine, serine, valine, tryptophan, and tyrosine;

(4) substituting the alanine at position 59 of SEQ ID NO: 2 with any one of cysteine, aspartic acid, glutamic acid, phenylalanine, glycine, histidine, isoleucine, lysine, leucine, methionine, asparagine, proline, glutamine, arginine, serine, threonine, valine, tryptophan, and tyrosine;

(5) substituting the glutamic acid at position 97 of SEQ ID NO: 2 with any one of alanine, cysteine, aspartic acid, phenylalanine, glycine, histidine, isoleucine, lysine, leucine, methionine, asparagine, proline, glutamine, arginine, serine, threonine, valine, tryptophan, and tyrosine; and (6) substituting the arginine at position 280 of SEQ ID NO: 2 with any one of alanine, aspartic acid, glutamic acid, cysteine, serine, phenylalanine, histidine, isoleucine, lysine, leucine, methionine, asparagine, proline, glutamine, threonine, valine, tryptophan, and tyrosine.

In a more preferred embodiment of the present invention, the amino acid substitution is selected from the group consisting of:

(1) substituting the threonine at position 8 of SEQ ID NO: 2 with aspartic acid, glutamic acid, tryptophan, or tyrosine;
(2) substituting the alanine at position 10 of SEQ ID NO: 2 with lysine or arginine;
(3) substituting the threonine at position 24 of SEQ ID NO: 2 with alanine, glycine, or serine;
(4) substituting the alanine at position 59 of SEQ ID NO: 2 with isoleucine, leucine, or valine;
(5) substituting the glutamic acid at position 97 of SEQ ID NO: 2 with asparagine; and/or,
(6) substituting the arginine at position 280 of SEQ ID NO: 2 with histidine or lysine.

In another preferred embodiment, the first 18 amino acids at the N-terminal of 5 sequences obtained through amino acid substitution on the basis of SEQ ID NO: 9, SEQ ID NO: 13, SEQ ID NO: 14, SEQ ID NO: 1, SEQ ID NO: 5 and SEQ ID NO: 16 are further deleted, and the amino acid sequences of the resulting mutants are shown in the sequence list as SEQ ID NOS: 25-29.

In another preferred embodiment, 5 or 10 amino acids at the C-terminal of 5 sequences obtained through amino acid substitution on the basis of SEQ ID NOS: 26-29 are further deleted, and the amino acid sequences of the resulting mutants are shown in the sequence list as SEQ ID NOS: 30-34.

In another preferred embodiment, further combinatorial mutagenesis is performed on the basis of the three mutants SEQ ID NOS: 14-16, and the amino acid sequence of the resulting mutant is shown in the sequence list as SEQ ID NO: 35. In another preferred embodiment, the first 18 amino acids at the N-terminal of 5 sequences obtained through amino acid substitution on the basis of SEQ ID NO: 9, SEQ ID NO: 13, SEQ ID NO: 14, SEQ ID NO: 1, SEQ ID NO: 5 and SEQ ID NO: 16 are further deleted, and the amino acid sequences of the resulting mutants are shown in the sequence list as SEQ ID NOS: 25-29.

In another preferred embodiment, the amino acid sequence of the resulting mutant is shown in the sequence list as SEQ ID NO: 36.

Preferably, the mutants of the present invention may be further mutated such that the sequence of the further mutated variant has at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to the sequence shown in SEQ ID NO: 2 at the same time functions as the immunoglobulin degrading enzyme IdeE.

The complete sequence of IdeE used in the present invention is publicly available as GenBank accession number ABF57910.1, the sequence of which is provided herein as SEQ ID NO: 1. This sequence includes the N-terminal methionine followed by a secretion signal sequence of 33 amino acids followed by the IdeE coding sequence. The N-terminal methionine and signal sequences are typically removed to form the mature IdeE protein, the sequence of which is provided herein as SEQ ID NO: 2. Unless otherwise stated, all references to numbering of amino acid positions in the immunoglobulin degrading enzyme sequences disclosed herein are based on the numbering of the corresponding positions in SEQ ID NO: 2 starting from the N-terminal.

The present invention also relates to a protein comprising the mutant of the present invention.

In a preferred embodiment, the protein comprises a signal peptide at the N-terminal of the mutant; preferably, the protein has a secretion signal sequence attached to the N-terminal of the mutant and a methionine attached to the N-terminal of the secretion sequence and/or a histidine tag attached to the C-terminal of the mutant; more preferably, the protein comprises or consists of from the N-terminal to the C-terminal: methionine, the secretion signal sequence, and the mutant.

II. Pharmaceutical Composition

The present invention relates to a composition comprising an immunoglobulin degrading enzyme mutant of the present invention or a protein comprising the mutant, and optionally a pharmaceutically acceptable carrier or excipient.

In a specific embodiment, the composition of the present invention further comprises an antibody, a small molecule targeted drug, and/or an Fc-containing protein.

In a specific embodiment, a target of the antibody is selected from the group consisting of a cell surface protein, cytokine, hormone, enzyme, intracellular messenger, intercellular messenger, and immune checkpoint.

In a specific embodiment, the composition of the present invention further comprises: a viral vector drug or a gene therapy drug, preferably the viral vector drug is selected from the group consisting of an oncolytic virus, a gene therapy virus, and a viral vector vaccine.

In a particular embodiment, the composition of the present invention further comprises: a drug capable of reducing the level of blood IgG, and preferably the drug capable of reducing the level of blood IgG is selected from the group consisting of an FcRn antibody, an Fc fragment variant with high affinity to FcRn.

2.1 Antibody

Preferably, in the composition as described above, the target of the antibody may be a cell surface protein, including but not limited to: AFP, av integrin, a4B7 integrin, BCMA, CD2, CD3, CD4, CD11a, CD19, CD20, CD22, CD25, CD30, CD32, CD33, CD36, CD38, CD40, CD46, CD47, CD52, CD56, CD64, CD70, CD74, CD79, CD80, CD86, CD105, CD121, CD123, CD133, CD138, CD174, CD205, CD227, CD326, CD340, CEA, c-Met, Cripto, CAIX, Claudin6, Claudin18.2, ED-B, EGFR, EpCAM, EphA2, EphB2, FAP, FOLR1, GD2, Globo H, GPC3, GPNMB, GPRC5D, HER-1, HER-2, HER-3, MAGE-A3, Mesothelin, MUC1, MUC4, MUC16, PSMA, TMEFF2, TAG-72, 5T4, ROR-1, Sca-1, SP, Trop-2, CD38, CGRP, IGF-1R, Nectin-4, P-Selectin, vWF, KLK, CCR4, SLAMF7, PCSK9, GD2, VEGFR2, BLyS, RANKL, α4β1 integrin, VEGFR, thromboglycoprotein Iib/IIIa, IFNAR1, TSLP, VEGF, or WT1.

The target of the antibody may be one or more cytokines, including but not limited to: interleukins IL-1 to IL-13, IL-1β, IL15, IL17, IL-23p19, IL2R, IL-5R, IL-6R, IL-17R, IL-2R, tumor necrosis factors α and β, interferons α, β and γ, VEGF, PDGF-α, FGF-23, Sclerostin, tumor growth factor β (TGF-β), colony stimulating factor (CSF), or granulocyte monocyte colony stimulating factor (GM-CSF).

The target of the antibody may be a hormone, enzyme, intracellular and intercellular messengers, such as: adenosine cyclase, guanosine cyclase, or phospholipase C.

The target of the antibody may be one or more of an immune checkpoint, including but not limited to: CTLA-4, PD-1, PD-L1, TIM-3, LAG3, Siglec7, Siglec9, Siglec15, 4-1BB, GITR, OX40, CD40L, CD28, TIGIT, VISTA.

The target of the antibody may be IgE, RSV F, neocornavirus, Dabigatran, FIX/FX, *Clostridium difficile* toxins B, C2, C5, anthrax PA.

The antibody may be selected from the group consisting of Satralizumab, Belantamab mafodotin, Tafasitamab, Inebilizumab, Sacituzumab govitecan, Isatuximab, Eptinezumab, Teprotumumab, Trastuzumab deruxtecan, Enfortumab Vedotin, Romosozumab, Crizanlizumab, Brolucizumab, Polatuzumab, Risankizumab, Caplacizumab, Emapalumab, Ravulizumab, Cemiplimab, galcanezumab, Fremanezumab, Moxetumomab Pasudotox, Lanadelumab, Mogamulizumab, Erenumab, Burosumab, Tildrakizumab, Ibalizumab, Emicizumab, Benralizumab, inotuzumab ozogamicin, Sarilumab, Guselkumab, Durvalumab, Dupilumab, Ocrelizumab, Avelumab, Brodalumab, Daclizumab, Bezlotoxumab, Olaratumab, Atezolizumab, Obiltoxaximab, Ixekizumab, Reslizumab, Idarucizumab, Mepolizumab, Elotuzumab, Necitumumab, Evolocumab, Alirocumab, Daratumumab, Dinutuximab, Secukinumab, Blinatumomab, Pembrolizumab, Nivolumab, Vedolizumab, Siltuximab, Ramucirumab, Obinutuzumab, Ado-Trastuzumab emtansine, Raxibacumab, Pertuzumab, Brentuximab vedotin, Belimumab, Ipilimumab, Tocilizumab, Denosumab, Denosumab, Ofatumumab, Canakinumab, Golimumab, Ustekinumab, Certolizumab pegol, Eculizumab, Panitumumab, Ranibizumab, Natalizumab, Bevacizumab, Cetuximab, Efalizumab, Tositumomab, Omalizumab, Adalimumab, Ibritumomab tiuxetan, Alemtuzumab, Gemtuzumab Ozogamicin, Trastuzumab, Infliximab, palivizumab, Basiliximab, Daclizumab, Rituximab, Abciximab, Catumaxomab, Muromomab.

2.2 Small Molecules Targeted Drug

Preferably, a composition as described above, wherein the composition further comprises a targeted drug selected from the group consisting of an epigenetic drug such as a histone deacetylase inhibitor, an inhibitor targeting the PI3K/Akt/mTOR signaling pathway such as Tricibine, and a tyrosine kinase inhibitor such as sunitinib, or a chemotherapeutic drug selected from the group consisting of an immunosuppressant such as cyclophosphamide, for example, thalidomide, pomalidomide, a proteasome inhibitor such as bortezomib, a cytotoxic drug such as gemcitabine, temozolomide, and a cell cycle non-specific drug such as mitoxantrone, or an immune checkpoint blocker.

2.3 Drug Capable of Reducing the Level of Blood IgG

Preferably, in the composition as described above, the polypeptide drug capable of reducing the level of blood IgG is capable of blocking the binding of blood IgG and FcRn proteins. Preferably, the polypeptide has a higher affinity to human FcRn protein than that of the blood IgG to human FcRn protein; the IgG is selected from the group consisting of IgG1, IgG2, IgG3, and IgG4. Preferably, the peptide comprises a variant of an antibody Fc fragment such as Efgartegimod, wherein the variant comprises a mutation capable of enhancing the affinity for Fc and FcRn, preferably YTE, YTEKF, LS, and NHS. The variant may be a monomer, a dimer, and a multimer. The positions of the mutations such as YTE, YTEKF, LS, and NHS used in the present invention are described by Dall'Acqua et al. (WF, D. A. et al, (2002). Journal of immunology (Baltimore, Md.: 1950) 169 (9): 5171-5180.) and Lee et al. (Lee, C. H. et al, (2019). Nat Commun 10 (1): 5031.). The mutant subject is selected from human IgG, and the IgG is selected from the group consisting of IgG1, IgG2, IgG3, and IgG4.

Other Fc fragment variants used in the present invention include, but are not limited to, the mutations described by Dall'Acqua et al. (WF, D. A. et al., (2002). Journal of immunology (Baltimore, Md.: 1950) 169 (9): 5171-5180.), mutations described by Shan et al. (Shan, L. et al., (2016). PLOS One 11 (8): e0160345.), mutations described by Lee et al., (Lee, C. H. et al., (2019). Nat Commun 10 (1): 5031.), mutations described by Mackness et al. (Mackness, B. C. et al., (2019). MAbs 11 (7): 1276-1288.), mutations described by Christophe et al., (Dumet Christophe, Pottier Jérémy, Gouilleux-Gruart Valérie et al., MAbs, 2019, 11:1341-1350.).

Preferably, the polypeptide comprises an antibody Fc fragment variant comprising a mutation capable of increasing affinity for Fc and FcγR, preferably an S239D/1322E, S239D/1322E/A330L, K326W/E333S, R214K mutation; the variant is preferably free of fucose modification. The variant may be a monomer, a dimer, and a multimer. Other Fc fragment variants used in the present invention include, but are not limited to, the mutations described by Wang et al., (Wang Xinhua., Mathieu Mary., Brezski Randall J. (2018). Protein Cell, 9 (1), 63-73. doi: 10.1007/s13238-017-0473-8).

Preferably, the variant comprising an affinity for Fc and FcRn comprises a mutation capable of increasing the affinity for Fc and FcγR. The variant may be a monomer, a dimer, and a multimer.

Preferably, the pharmaceutical combination as described above, wherein the polypeptide is selected from anti-FcRn antibodies such as Nipocalimab, Rozanolixizumab, RVT-1401, HBM9161, ALXN1830, SYNT001, and Nirsevimab.

Preferably, the pharmaceutical combination as described above, wherein the polypeptide is selected from small peptide fragments capable of specifically binding to FcRn, the small peptide fragments being 10-70 amino acids in length, such as ABY-039.

Preferably, the polypeptide is selected from Fc multimers that specifically bind to FcRn, such as GL-2045, M230, PRIM, HexaGardTM, CSL777, and Hexavalent molecules by UCB.

Preferably, the polypeptide includes, but is not limited to, the polypeptide fragments described by Sockolosky et al., (Sockolosky Jonathan T, Szoka Francis C. Adv. Drug Deliv. Rev., 2015, 91:109-24).

2.4 Viral Vector Drug

Preferably, in the composition as described above, in the viral vector drug, the virus used for the viral vector drug is selected from ssDNA viroid, dsDNA viroid, ssRNA viroid, and dsRNA viroid; and/or the virus used for the viral vector drug is selected from a wild-type virus strain or a naturally attenuated strain, a genetically engineered selectively attenuated strain, a gene-loaded virus strain, and a gene transcription targeted virus strain.

Preferably, the wild-type strain or naturally attenuated strain is selected from Newcastle disease virus, reovirus, mumps virus, west Nile virus, adenovirus, vaccinia virus, etc.

Preferably, the genetically engineered selectively attenuated strains such as ONYX-015, and G207, achieve tumor selectivity for viral replication by artificially deleting key genes, e.g. Thymidine kinase (TK) knockout genetically engineered human herpes simplex virus I (HSV-1). ONYX-015 deleted 827 bp in the E1b region and made a point mutation in the gene for E1B55K protein to prematurely terminate its expressed gene and fail to express E1B55K protein. G207 deleted the γ34.5 gene, which is the neurotoxicity determinant of HSV-1.

Preferably, the gene-loaded strain, such as JX-594 or T-VEC, is loaded with an exogenous gene, such as granulocyte macrophage-colony stimulating factor (GM-CSF).

Preferably, the gene transcription targeted viral strain, for example G92A, involves inserting tissue or tumor-specific promoters before the essential genes of the virus to control the replication of oncolytic viruses within tumor cells.

Preferably, in the pharmaceutical combination as described above, the ssDNA viroid is selected from parvovirus, preferably the H-1PV virus.

Preferably, the dsDNA viroid is selected from herpes simplex virus, adenovirus, and poxvirus; more preferably, the herpes simplex virus is preferably herpes simplex virus type I HSV-1, such as R3616, T-VEC, HF10, G207, NV1020, orienX010, and the poxvirus is selected from Pexa-Vec (vaccinia virus), JX-594 (vaccinia virus), GL-ONC1, Myxoma; the adenovirus is selected from Enadenotucirev, DNX-2401, C-REV, NG-348, prosAtak, CG0070, ADV-TK, EDS01, KH901, H101, H103, VCN-01, Telomelysin (OBP-301).

Preferably, the ssRNA viroid is selected from Picornavirus, alphavirus, Retroviruses, Paramyxoviruses, Rhabdoviruses; preferably, the Picornavirus is selected from CAVATAK, PVS-RIPO, CVA21 (enterovirus), RIGVIR; the alphavirus is selected from M1, Sindbis AR339, Semliki Forest virus; the Retroviruses is selected from Toca511; the Paramyxoviruses is selected from MV-NIS, PV701 (Newcastle disease virus); the Rhabdoviruses is selected from VSV-IFN β, MG1-MAGEA3, VSV-GP.

Preferably, the dsRNA viroid is selected from Reoviruses; preferably, the Reoviruses is selected from Pelareorep, Reolysin, vaccinia virus, mumps virus, and human immunodeficiency virus (HIV); preferably, the RNA viroid is selected from reovirus, coxsackievirus, polio virus, seneca valley virus, measles virus, Newcastle disease virus, vesicular stomatitis virus, and influenza virus.

Preferably, the pharmaceutical combination as described above, wherein the oncolytic virus expresses an exogenous gene, preferably a Bispecific T cell engager (BiTE), an scFv fragment, a cytokine, and a chemokine. The BiTE can bind to molecules activating T cells such as CD3, and at the same time can bind to an antigen target on the surface of a cancer cell; the scFv targets an immune checkpoint; the immune checkpoints include CTLA-4, PD-1, TIM-3, LAG3, Siglec15, 4-1BB, GITR, OX40, CD40L, CD28, TIGIT, and VISTA. The cytokine and chemokine can be e.g., GM-CSF, interleukin-2 (IL-2), interleukin-12 (IL-12), interleukin-15 (IL-15), interferons (IFN), tumor necrosis factor (TNF), soluble CD80, and CCL3.

In some embodiments, the viral drug carrier is preferably an AAV virus, such as AAV1, AAV2, AAV3, AAV4, AAV5, AAV6, AAV7, AAV8, AAV9, AAV10, AAV3B, AAV-218, Rh10, and Rh74.

In some embodiments, the viral drug carrier is preferably an adenovirus, lentivirus, or retrovirus.

The viral vector drug and/or immunoglobulin degrading enzyme variant can be encapsulated or fused with liposomes, nanoparticles, lipid nanoparticles, polymers, microparticles, microcapsules, mouselles, or exosomes.

2.5 Gene Therapy Drug

Preferably, in the composition as described above, the gene therapy virus expresses an exogenous gene encoding a protein required for a gene deficient disease selected from acid α-glucosidase, copper transport ATPase2, α galactosidase, arginine succinate synthase, β-glucocerebrosidase, β-hexosaminidase A, Cl protease inhibitor or Cl esterase inhibitor, glucose 6 phosphatase, insulin, glucagon, growth hormone, parathyroid hormone, growth hormone releasing factor, follicle stimulating hormone, luteinizing hormone, human chorionic gonadotropin, vascular endothelial growth factor, angiogenin, angiostatin, granulocyte colony stimulating factor, erythropoietin, connective tissue growth factor, basic fibroblast growth factor, acidic fibroblast growth factor, epidermal growth factor, transforming growth factor a, platelet-derived growth factor, insulin growth factors I and II, TGF, bone morphogenetic protein, nerve growth factor, brain-derived neurotrophic factor, neurotrophins NT-3 and NT4/5, ciliary neurotrophic factor, glial cell line-derived neurotrophic factors, neurotrophins, lectins, netrin-1 and netrin-2, hepatocyte growth factor, ephrins, tyrosine hydroxylase, thrombopoietin, interleukins (IL-1 to IL-36, etc.), monocyte chemotactic protein, leukemia inhibitory factor, granulocyte macrophage protein colony stimulating factor, Fas ligand, tumor necrosis factors a and b, interferons a/b/g, stem cell factor, flk-2/flt3 ligand, IgM, IgA, IgD, and IgE, chimeric immunoglobulin, humanized antibody, single chain antibody, T cell receptor, chimeric T cell receptor, single chain T cell receptor, class I and class II MHC molecule, cystic fibrosis transmembrane regulator protein, coagulation factors (factor XIII, factor IX, factor VIII, factor X, factor VII, factor VIIa, protein C, etc.), retinal pigment epithelium-specific 65 kDa protein, LDL receptor, lipoprotein lipase, ornithine transcarbamylase, β-globin, α-globin, spectrin, α-antitrypsin adenosine deaminase, metal transporters (ATP 7A or ATP7), sulfonamidases, enzymes involved in lysosomal storage diseases (ARSA), hypoxanthine guanine phosphoribosyl transferase, b-25 glucocerebrosidase, sphingomyelinase, lysosomal hexosaminidase, and branched-chain ketoacid dehydrogenase.

Preferably, in the composition as described above, the gene therapy virus carries an exogenous gene encoding an inhibitory nucleic acid selected from siRNA, an antisense molecule, miRNA, RNAi, ribozymes, and shRNA. The inhibitory nucleic acid binds to a gene associated with a polynucleotide repeat disease, a transcript of the gene, or a polynucleotide repeat of the transcript of the gene. The disease gene encodes a protein of interest selected from a subtype selected from HTT, the androgen receptor on the X chromosome of bulbar muscular atrophy, human Ataxin-1/-2/-3/-7, Cav2.1P/Q voltage-dependent calcium channel (CACNA 1A), TATA-binding protein, Ataxin8 reverse chain (ATXN8OS), serine/threonine protein phosphatase 2A55 kDa spinocerebellar ataxia, subtype B subtype beta (types 1, 2, 3, 6, 7, 8, 1217), FMR1 (fragility of fragile X syndrome 1), FMR1 of fragile X-associated tremor/ataxia syndrome (fragile X mental retardation 1), FMR1 of fragile XE mental retardation (fragile X mental retardation 2) or AF4/FMR2 family member 2; troponin kinase in myotonic dystrophy (MT-PK), and Frataxin. The disease gene is selected from a mutant of the superoxide dismutase 1 (SOD1) gene, a gene involved in the pathogenesis of Parkinson's disease and/or Alzheimer's disease, apolipoprotein B (APOB), PCSK9, a gene associated with HIV infection (HIVTat, TAR, HIVTAR, or CCR5), an influenza A virus genome/gene sequence in influenza virus infection, a severe acute respiratory syndrome (SARS) coronavirus genome/gene sequence in SARS infection, respiratory syncytial virus genome/gene sequence in respiratory syncytial virus infection, ebola virus genome/gene sequence in ebola virus infection, hepatitis B and C virus genome/gene sequence in hepatitis B and C virus, herpes simplex virus (HSV) genome/gene sequence of HSV infection, coxsackie virus B3 genome/gene sequence of coxsackie virus B3 infection, silencing genes in primary dystonia (allele-specific silencing) such as torsinA, specific pan-class I and HLA alleles in transplants, mutations in autosomal dominant retinitis pigmentosa, and rhodopsin genes.

III. Product and Kit

The invention also provides a product comprising the mutant, protein, and/or composition of the present invention and an additional therapeutic agent; the additional therapeutic agent is selected from a viral vector drug, an antibody, and a polypeptide drug capable of reducing the level of blood IgG.

The present invention also provides a kit or kit-of-parts comprising: 1) a therapeutically effective amount of a drug comprising the mutant, protein, and/or composition of the present invention; and 2) a therapeutically effective amount of the additional therapeutic agent; the therapeutic agent is selected from the group consisting of a viral vector drug, an antibody, a polypeptide drug capable of reducing the level of blood IgG; the viral vector drug is preferably an oncolytic virus, a gene therapy virus. The kit may further comprise 3) a targeted drug or chemotherapeutic drug or an immune checkpoint blocker. The targeted drug selected from the group consisting of an epigenetic drug such as a histone deacetylase inhibitor, an inhibitor targeting the PI3K/Akt/mTOR signaling pathway such as Tricibine, and a tyrosine kinase inhibitor such as sunitinib, or a chemotherapeutic drug selected from the group consisting of an immunosuppressant such as cyclophosphamide, for example, thalidomide, pomalidomide, a proteasome inhibitor such as bortezomib, a cytotoxic drug such as gemcitabine, temozolomide, and a cell cycle non-specific drug such as mitoxantrone, or an immune checkpoint blocker.

The kit or kit-of-parts comprises kit A comprising a therapeutically effective amount of the mutant, protein, and/or composition of the present invention, and kit B comprising a therapeutically effective amount of the additional therapeutic agent; the therapeutic agent is selected from an viral vector drug, an antibody, a polypeptide drug capable of reducing the level of blood IgG; the viral vector drug is preferably an oncolytic virus, a gene therapy virus. The kit-of-parts may further comprise kit C. Kit C includes a targeted drug or a chemotherapeutic drug or an immune checkpoint blocker. The targeted drug selected from the group consisting of an epigenetic drug such as a histone deacetylase inhibitor, an inhibitor targeting the PI3K/Akt/mTOR signaling pathway such as Tricibine, and a tyrosine kinase inhibitor such as sunitinib, or a chemotherapeutic drug selected from the group consisting of an immunosuppressant such as cyclophosphamide, for example, thalidomide, pomalidomide, a proteasome inhibitor such as bortezomib, a cytotoxic drug such as gemcitabine, temozolomide, and a cell cycle non-specific drug such as mitoxantrone, or an immune checkpoint blocker.

The kit can comprise instructions relating to the administration (e.g. dosage information, dosing interval information) of a therapeutically effective amount of the mutant, protein, and/or composition of the present invention and a therapeutically effective amount of the additional therapeutic agent. The additional therapeutic agent is selected from a viral vector drug, an antibody, or a polypeptide drug capable of reducing the level of blood IgG; the viral vector drug is preferably an oncolytic virus, a gene therapy virus.

Well-established expression systems can be used to manufacture the viral vector drug. Some exemplary methods include the use of mammalian cell expression systems to produce viral particles, such as the use of HEK293 cells for the production of adenoviral viroid vector drugs (Freedman Joshua D, Duffy Margaret R, Lei-Rossmann Janet et al., An Oncolytic Virus Expressing a T-cell Engager Simultaneously Targets Cancer and Immunosuppressive Stromal Cells. [J].Cancer Res., 2018, 78:6852-6865).

The pharmaceutical carrier may be a liquid and the pharmaceutical composition may be in the form of a solution. Liquid carriers are used in preparing solutions, suspensions, emulsions, syrups, elixirs, and pressurized compositions. The active ingredient can be dissolved or suspended in a pharmaceutically acceptable liquid carrier such as water, an organic solvent, a mixture of both, or pharmaceutically acceptable oils or fats.

Pharmaceutical compositions for parenteral administration are sterile, substantially isotonic, and pyrogen-free and are prepared according to GMP by FDA or similar administrations. The viral vector drug may be administered as an injectable dosage form of a solution or suspension of the substance in a physiologically acceptable diluent and a pharmaceutical carrier which may be a sterile liquid such as water, oil, saline, glycerol, or ethanol. In addition, auxiliary substances, such as wetting or emulsifying agents, surfactants, pH buffering substances, and the like, may be present in the compositions. Other components of pharmaceutical compositions include petroleum, animal, plant, or synthetic sources such as peanut oil, soybean oil, and mineral oil. In general, glycols such as propylene glycol or polyethylene glycol are preferred liquid carriers, particularly for injectable solutions. Viral vector drugs can be administered in depot injections or implant formulations which can be formulated to permit sustained release of the active ingredient. Usually, the composition is prepared into an injectable substance, i.e. a liquid solution or suspension. It can also be prepared in a solid form suitable for dissolution or suspension in liquid carriers before injection.

IV. Use of Mutant, Protein, Pharmaceutical Composition and Kit

The present invention also relates to the use of the mutant, protein, composition, and/or kit of the present invention in the preparation of drugs. In some embodiments, the drug is used for treating an autoantibody-mediated disorder in a subject. In some embodiments, the drug is used for reducing the level of IgG in a subject. In some embodiments, the drug is used for preventing and/or treating autoantibody-mediated organ rejection following solid organ transplantation in a subject. In some embodiments, the drug is used for gene therapy. In some embodiments, the drug is used for eliminating neutralizing antibodies from pre-existing antiviral vectors in the body prior to viral vector-based gene therapy. In some embodiments, the drug is used for treating a tumor in a subject. In some embodiments, the drug is used for clearing autoantibodies in a subject so that the Fc-containing agent is more therapeutically effective. In some embodiments, the drug is used for reducing serum levels of an Fc-containing agent in a subject to whom the Fc-containing agent has been administered.

In a preferred embodiment, the mutant, protein, composition, and/or kit of the present invention can be used for IgG analysis. Among other things, the Fc and F(ab')2 fragments obtained after cleavage of IgG using the mutant, protein, composition, and/or kit of the present invention are used for, e.g. mass spectrometry molecular weight analysis, glycoform modification analysis, ADC molecular analysis, etc.

In another preferred embodiment, the mutant, protein, composition, and/or kit of the present invention may also be used to prepare an Fab antibody fragment. Wherein the Fab fragment is prepared by reduction of F(ab')2 fragments generated after cleavage of IgG using the mutant, protein, composition, and/or kit of the present invention.

4.1 Autoantibody-Mediated Disorder

The present invention relates to the use of the mutant, protein, composition, and/or kit of the present invention in the preparation of a drug for treating an autoantibody-mediated disorder in a subject. In some embodiments, the autoantibody-mediated disorder is an autoimmune disease and/or a pathogenic antibody-mediated disease or disorder.

Preferably, the disease is a pathogenic antibody-mediated disease or disorder, including, but not limited to, autoimmune diseases or conditions mediated by pathogenic IgG, such as Addison's disease, alopecia areata, ankylosing spondylitis, antiphospholipid syndrome, aplastic anemia, anti-GBM glomerulonephritis, anti-NMDAR encephalitis, antiphospholipid syndrome, autoimmune gastritis, autoimmune hearing loss, autoimmune hemolytic anemia, autoimmune hepatitis, autoimmune hypoparathyroidism, autoimmune hypophysitis, autoimmune inner ear disease, autoimmune lymphoproliferative syndrome, autoimmune myocarditis, autoimmune oophoritis, autoimmune bullous skin disease, autoimmune orchitis, autoimmune polyendocrinopathy, Behcet's disease, bullous pemphigoid, cardiomyopathy, inflammatory demyelinating polyneuropathy, acute motor axonal neuropathy, Churg-Strauss syndrome, coeliac disease, autoimmune urticaria, Crohn's disease, CREST syndrome, celiac disease, Degos's disease, anti-neutrophil cytoplasmic antibody associated vascular inflammation, autoimmune neutropenia, acquired epidermolysis bullosa, essential mixed cryoglobulinemia, giant cell arteritis, glomerulonephritis, Goodpasture's syndrome, Graves' disease, Guillain-Barre syndrome, Hashimoto's thyroiditis, primary immunologic thrombocytopenia purpura, inflammatory bowel disease, Kawasaki disease, Ménière's syndrome, mixed connective tissue disease, Mooren ulcer, rheumatoid arthritis, multiple sclerosis, myasthenia gravis, stiffman syndrome, complete congenital heart block, acquired epidermolysis bullosa, pemphigus *foliaceus*, pemphigus vulgaris, pernicious anemia, polyarteritis nodosa, types of polyglandular autoimmune syndrome, primary biliary cirrhosis, types of polyglandular autoimmune syndrome, types of polyglandular autoimmune syndrome, polymyositis/dermatomyositis, psoriasis, psoriatic arthritis, Raynaud's syndrome, Reiter's syndrome, rheumatic heart disease, hemophilia-acquired FVIII deficiency, Lambert-Eaton myasthenia syndrome, multiple myeloma, sarcoidosis, collagen thesaurismosis, Sjogren's syndrome, subacute thyroiditis, sympathetic ophthalmia, systemic lupus erythematosus, Takayasu's arteritis, Sjögren's syndrome, type I diabetes, vitiligo, Vogt-Koyanagi-Harada syndrome or Wegener's granulomatosis, acute asthma or chronic asthma, organ transplant rejection, primary progressive multiple sclerosis, systemic sclerosis, seropathy, and immune complex hypersensitivity.

Host IgG causes acute transplant rejection in organ transplantation. Transplant rejection is divided into two cases, one is host versus graft reaction (HVGR) and the other is graft versus host reaction (GVHR). In solid organ transplants, host versus graft reactions are predominant and graft versus host reactions are rare. In bone marrow transplantation, graft-versus-host reactions are common.

Graft-versus-host reaction (GVHR) refers to the recognition by the recipient's immune system of a graft, such as a foreign tissue or organ, as a heterologous component after the recipient has undergone an allograft or organ transplant, which initiates an immunological response to the attack, destruction, and clearance of the graft. For patients with high sensitivity to human lymphocyte antigen (HLA), transplant rejection is more likely to occur. The mechanism of rejection mainly includes two aspects: cellular immunity and humoral immunity, in which humoral immunity is the immune mechanism of IgG produced by effector B cells for the purpose of protection.

The present invention relates to the use of the mutant, protein, composition, and/or kit of the present invention in the preparation of a drug for preventing and/or treating autoantibody-mediated organ rejection following solid organ transplantation in a subject. In some embodiments, organ rejection includes but is not limited to, allograft rejection in organ transplantation such as kidney transplant rejection, allogeneic islet transplant rejection, pancreas transplant rejection, heart transplant rejection, liver transplant rejection, lung transplant rejection, or small bowel transplant rejection.

Diseases or conditions mediated by pathogenic antibodies also include hyperglobulinemia. Wherein the hyperglobulin is produced by leukocytes selected from the group consisting of B cells and abnormal B cells; the globulin comprises a gamma globulin; the hyperglobulinemia comprises primary monoclonal gammaglobulinemia, connective tissue disease, liver disease, infectious disease, sarcoidosis, myasthenia gravis, Hodgkin's disease, Behcet's disease, nephritis, allergic purpura, immune (or idiopathic) thrombocytopenia, malignant monoclonal gammaglobulinemia (such as multiple myeloma, heavy chain disease, malignant lymphoma, chronic lymphocytic leukemia, macroglobulinemia, etc.), secondary monoclonal gammaglobulinemia (such as non-lymphoreticular tumor, monocytic leukemia, cryoglobulinemia, etc.), benign M-proteinemia, monoclonal gammopathy of unknown significance (MGUS), Waldenstrom's macroglobulinemia, AL-type amyloidosis, solitary plasmacytoma (bone or extraosseous), POMES syndrome, reactive plasmacytosis, osteolytic lesions of metastatic cancer, plasmoblastic lymphoma, monoclonal immunoglobulin-associated renal damage (MGRS), etc. The condition is preferably multiple myeloma.

The invention also relates to the use of the mutant, protein, composition, and/or kit of the present invention in the preparation of a drug for the treatment or prevention of a disease. Preferably, the disease includes but is not limited to, tumors, cancers, infectious diseases, gene-deficient diseases, diseases, or conditions mediated by pathogenic IgG antibodies. Such infectious diseases include viral, bacterial, or fungal infections.

4.2 Tumors or Cancers

The tumor or cancer is selected from the group consisting of: acute lymphoblastic leukemia, acute myeloid leukemia, adrenocortical carcinoma, AIDS-associated cancer, AIDS-associated lymphoma, anal carcinoma, appendiceal carcinoma, astrocytoma, cerebellar or cerebral carcinoma in children, basal cell carcinoma, extrahepatic cholangiocarcinoma, bladder cancer, bone cancer, osteosarcoma/malignant fibrous histiocytoma, brain stem glioma, brain cancer, brain tumor-cerebellar astrocytoma, brain tumor-cerebral astrocytoma/malignant glioma, brain tumor-ependymoma, brain tumor-medulloblastoma, brain tumor-supratentorial primitive neuroectodermal tumor, brain tumor-visual pathway and hypothalamic glioma, breast cancer, bronchial adenoma/carcinoid, Burkitt lymphoma, carcinoid tumor, unidentified primary cancer, central nervous system lymphoma, cerebellar astrocytoma, cerebral astrocytoma/malignant glioma, cervical cancer, chronic lymphocytic leukemia, chronic myeloid leukemia chronic myeloproliferative disorder, colon cancer, cutaneous T-cell lymphoma, desmoplastic small round cell tumor, endometrial cancer, ependymoma, esophageal cancer, Ewing's sarcoma in the Ewing's tumor family, extracranial germ cell tumor, extragonadal germ cell tumor in children, extrahepatic biliary tract cancer, eye cancer-intraocular melanoma, eye cancer-retinoblastoma, gall bladder cancer, gastric cancer, gastrointestinal carcinoid tumor, gastrointestinal GIST, extracranial, extragonadal, or ovarian germ cell tumor, gestational trophoblastic tumor, brain stem glioma, childhood astrocytoma glioma, visual pathway and hypothalamic glioma in children, gastric carcinoid, hairy cell leukemia, head and neck cancer, heart cancer, hepatocellular (liver) cancer, Hodgkin's lymphoma, hypopharyngeal cancer, hypothalamic and visual pathway glioma, intraocular melanoma, islet cell cancer (endocrine pancreas), Kaposi's sarcoma, renal cancer (renal cell carcinoma), laryngeal cancer, leukemia, acute lymphoblastic leukemia (also known as acute lymphocytic leukemia), acute myeloid leukemia (also known as acute myeloid leukemia), chronic lymphocytic leukemia (also known as chronic lymphocytic leukemia), chronic myeloid leukemia (also known as chronic myeloid leukemia), hairy cell leukemia, lip and oral cancer, liposarcoma, liver cancer (primary), non-small cell lung cancer, small cell lung cancer, lymphoma, cutaneous T-cell lymphoma, Hodgkin's lymphoma, non-Hodgkin's lymphoma (old classification: all lymphomas except Hodgkin's lymphoma), primary central nervous system lymphoma, macroglobulinemia, malignant fibrous histiocytoma/osteosarcoma of bone, medulloblastoma, melanoma, intraocular (ocular) melanoma, Merkel cell carcinoma, mesothelioma, adult malignant mesothelioma, primary occult metastatic squamous neck cancer, oral cancer, multiple endocrine neoplasia syndrome, mycosis fungoides, myelodysplastic syndrome, myelodysplastic/myeloproliferative disorders, chronic myelogenous leukemia, adult acute myeloid leukemia, acute myeloid leukemia, myeloproliferative disorder, nasal and paranasal sinus carcinoma, nasopharyngeal carcinoma, neuroblastoma, non-Hodgkin's lymphoma, oral cancer, oropharyngeal cancer, osteosarcoma/malignant fibrous histiocytoma of bone, ovarian cancer, epithelial ovarian cancer (surface epithelial-mesenchymal cell tumor), ovarian germ cell tumor, low-grade malignant potential tumor of ovary, pancreatic cancer, pancreatic islet cell carcinoma, paranasal sinus and nasal cavity cancer, parathyroid carcinoma, penile carcinoma, pheochromocytoma, pineal astrocytoma, pineal germ cell tumor, pinealoblastoma and supratentorial primitive neuroectodermal tumor, pituitary tumor, plasmacytoma/multiple myeloma, pleuropulmonary blastoma, primary central nervous system lymphoma, prostate cancer, rectal cancer, renal pelvis and ureter renal cell carcinoma (renal carcinoma), transitional cell carcinoma, retinoblastoma, rhabdomyosarcoma, salivary gland carcinoma, Ewing's family tumour sarcoma, kaposi's sarcoma, soft tissue sarcoma, uterine sarcoma, Sézary syndrome, skin cancer (non-melanoma), skin cancer (melanoma), Merkel cell skin cancer, small cell lung cancer, small bowel cancer, soft tissue sarcoma, squamous cell carcinoma, primary occult squamous neck cancer, metastatic gastric cancer, supratentorial primitive neuroectodermal tumors, cutaneous T-cell lymphoma (see mycosis fungoides and Sézary syndrome), testicular cancer, throat cancer, thymoma, thymoma and thymic adenocarcinoma, thyroid cancer, thyroid cancer, renal pelvis and ureter transitional cell carcinoma, ureter and renal pelvis trophoblastic tumors, transitional cell carcinoma of the urinary tract, endometrial uterine cancer, uterine sarcoma, vaginal cancer, visual pathway and hypothalamic glioma, vulval cancer, macroglubinemia and nephroblastoma (renal carcinoma).

4.3 Cancers or Infectious Diseases

The cancer or infectious disease may be a veterinary disease or a human disease, as exemplified below:

| Recombinant viral vector | Cancers and Infectious Diseases | |
|---|---|---|
| | Animals | Human |
| Adenovirus | Avian influenza virus, Mycobacterium tuberculosis, and foot and mouth disease virus | *Plasmodium falciparum*, *Mycobacterium tuberculosis*, influenza virus, HIV-1, hepatitis C virus, coronavirus |
| Shigella phage | None | *Mycobacterium tuberculosis* |
| Canary attenuated virus | Equine influenza virus, west Nile virus, rabies virus, feline leukemia virus, canine distemper virus | HIV-1, cancer |
| Avipox virus | Avian influenza virus, Avipox virus, Newcastle disease virus | Cancer |
| Newcastle disease virus | Avian influenza virus, Newcastle disease virus | None |
| Turkey herpesvirus | Infectious bursal disease virus, Marek's disease virus | None |
| Attenuated yellow fever virus strain 17D | West Nile virus | West Nile virus, dengue virus, Japanese encephalitis virus |
| Lentivirus | None | Melanoma, HIV-1 |
| Measles virus | None | *Plasmodium falciparum*, human papilloma virus |
| Modified vaccinia Ankara virus | *Mycobacterium bovis* | *Plasmodium falciparum*, mycobacterium tuberculosis, influenza A virus, colon cancer, kidney cancer, lung cancer, prostate cancer |
| New York attenuated vaccinia virus | None | *Plasmodium falciparum*, HIV-1 |
| Hemagglutinating virus of Japan | None | HIV-1 |
| Vaccinia virus | Rabies virus | Cancer |

4.4 Gene Deficiency-Related Diseases

The Gene deficiency-related diseases, include, but not limited to, protein overexpression, loss of protein expression, heterologous protein expression resulting from viral infection; preferably, the gene therapy drug is used to treat gene overexpression or gene underexpression or gene deficiency or infectious diseases; the disease is selected from pulmonary diseases (e.g. cystic fibrosis), hemorrhagic diseases (e.g. hemophilia A or hemophilia B with or without inhibitors), thalassemia, blood diseases (e.g. anemia), Alzheimer's disease, Parkinson's disease, Huntington's disease, amyotrophic lateral sclerosis (ALS), epilepsy, lysosomal storage diseases (e.g. aspartyl glucosuria, Batten's disease, late infantile neuronal lipid brown disease type 2 (CLN2), cystinosis, Fabry's disease, Gaucher's I, II and III types, glycogen storage disease II (Pompe's disease), GM2-gangliopathy type I (Tay Sachs's disease), GM2-gangliopathy type II (Sandhoff's disease), mucosal seborrheic diseases type I (salivary intoxication type I and II, type II (I cell disease), type III (pseudo Hurler's disease) and IV, mucopolysaccharide storage disease (Hurler's disease and variation, Hunter, Sanfilippo types A and B), C, D, Morquio types A and B, Maroteaux-Lamy and Sly's disease), Niemann-Pick diseases types A/B, C1, and C2, and Schindler diseases types I and II), hereditary angioedema (HAE), disorders of copper or iron accumulation (e.g. Wilson's disease or Menkes disease), lysosomal acid lipase deficiency, neurological or neurodegenerative diseases, cancer, type 1 or 2 diabetes, adenosine deaminase deficiency, metabolic defects (e.g. glycogen storage disease), solid organs (e.g. brain, liver, kidney, heart) or infectious viruses (e.g. hepatitis B and C, HIV etc.), bacterial or fungal diseases; coagulation disorder.

Preferably, wherein the subject has hemophilia A, hemophilia A with inhibitory antibodies, hemophilia B, hemophilia B with inhibitory antibodies, any blood coagulation factor: VII, VIII, IX, X, XI, V, XII, II, von Willebrand factor or FV/FVIII combined deficiency, thalassemia, vitamin K epoxyreductase C1 deficiency, or y-carboxylase deficiency.

Preferably wherein the disease caused by the genetic defect is anemia, bleeding associated with trauma, injury, thrombosis, thrombocytopenia, stroke, coagulopathy, disseminated intravascular coagulation (DIC); excessive anticoagulation associated with heparin, low molecular weight heparin, pentasaccharide, warfarin, small molecule antithrombotic agents (i.e. FXa inhibitors), or platelet disorders (e.g. Bernard Soulier syndrome, Glanzmann blood deficiency, or reservoir deficiencies).

4.5 Drug Administration and Treatment Method

The present invention also relates to a method of administering the mutant, protein, pharmaceutical composition, and/or kit of the present invention, and a method of administering the mutant, protein, pharmaceutical composition, and/or kit of the present invention to treat a disease or disorder.

Preferably, the mutant, protein, and/or composition of the present invention can be administered prior to administration of an additional therapeutic agent that has produced or is susceptible to producing an anti-drug antibody in the body.

Preferably, the mutant, protein, and/or composition of the present invention may be administered prior to, simultaneously with, and/or after administration of an additional therapeutic agent that has produced or is susceptible to producing an anti-drug antibody in the body.

In the use of the present invention, the mutant, protein, and/or composition of the present invention and the additional therapeutic agent(s) are present as a combined preparation for simultaneous, separate, or sequential use.

In some embodiments, the method comprises the steps of: 1) administering the mutant, protein, and/or composition of the present invention to a subject; and subsequently, 2) administering the additional therapeutic agent to the subject. Preferably, the mutant, protein, and/or composition of the present invention are separated in time from the administration of the additional therapeutic agent.

In some embodiments, the method comprises the steps of: 1) administering the additional therapeutic agent to the subject; and subsequently, 2) administering the mutant, protein, and/or composition of the present invention to the subject. Preferably, the mutant, protein, and/or composition of the present invention are separated in time from the administration of the additional therapeutic agent.

Preferably, the mutant, protein, and/or composition of the present invention is administered in amounts and at intervals sufficient to reduce immunoglobulin levels in the subject to 60% of the starting level. More preferably, the mutant, protein, and/or composition of the present invention is administered in an amount and at a time interval sufficient to reduce binding of immunoglobulin levels in the subject to less than 50%, 40%, 30%, 20%, or 10% of the starting level in the patient. The mutant, protein, and/or composition of the present invention may be administered at a single-point in time or within a set period of time.

Preferably, the mutant, protein, and/or composition of the present invention is administered by intravenous infusion, intraperitoneal injection, intramuscular injection, articular injection, intradermal injection, or subcutaneous injection, the preferred mode of injection is intravenous infusion. And/or the amount of mutant, protein, and/or composition of the present invention administered is 0.01 mg/kg body weight to 2 mg/kg body weight, 0.04 to 2 mg/kg body weight, 0.12 mg/kg body weight to 2 mg/kg body weight, 0.24 mg/kg body weight to 2 mg/kg body weight or 1 mg/kg body weight to 2 mg/kg body weight.

Preferably, the mutant, protein, and/or composition of the present invention and the additional therapeutic agent are administered at a time interval of at least 30 minutes, at least 1 hour, at least 2 hours, at least 3 hours, at least 4 hours, at least 4 hours, at least 5 hours, or at least 6 hours; and up to 35 days, up to 28 days, up to 21 days, up to 18 days, up to 14 days, up to 13 days, up to 12 days, up to 11 days, up to 10 days, up to 9 days, up to 8 days, up to 7 days, up to 6 days, up to 5 days, up to 4 days, up to 3 days, up to 2 days, up to 24 hours, up to 18 hours, up to 12 hours, up to 10 hours, up to 8 hours, up to 7 hours, or up to 6 hours.

Preferred, the time interval between the mutant, protein, and/or composition of the present invention and the additional therapeutic agent is from 30 minutes to 1 hour, from 30 minutes to 2 hours, from 30 minutes to 3 hours, from 30 minutes to 4 hours, from 30 minutes to 5 hours, from 30 minutes to 6 hours, from 1 to 2 hours, from 1 to 3 hours, from 1 to 4 hours, from 1 to 5 hours, from 1 to 6 hours, from 2 to 3 hours, from 2 to 4 hours, from 2 to 5 hours, from 2 to 6 hours, from 3 to 4 hours, from 3 to 5 hours, from 3 to 6 hours, from 4 to 5 hours, from 4 to 6 hours, or from 5 to 6 hours.

In yet another embodiment, the method comprises the steps of 1) ex vivo treating blood from the subject with the mutant, protein, and/or composition of the present invention; 2) returning th blood to the subject; and 3) administering the additional therapeutic agent to the subject.

In yet another embodiment, the method comprises the steps of: 1) administering the additional therapeutic agent to the subject; 2) ex vivo treating the blood from the subject with the mutant, protein, and/or composition of the present invention; and 3) returning the blood to the subject.

In a preferred embodiment, the mutant, protein, and/or composition of the present invention are used in combination with an additional therapeutic agent for the prevention and/or treatment of cancers.

In a preferred embodiment, the mutant, protein, and/or composition of the present invention is used in combination with an additional therapeutic agent for the prevention and/or treatment of viral infections.

In a preferred embodiment, the mutant, protein, and/or composition of the present invention is used in combination with an additional therapeutic agent for the prevention and/or treatment of bacterial infections.

In a preferred embodiment, the mutant, protein, and/or composition of the present invention are used in combination with an additional therapeutic agent for the prevention and/or treatment of fungal infections.

In a preferred embodiment, the mutant, protein, and/or composition of the present invention are used in combination with an additional therapeutic agent for the prevention and/or treatment of diseases associated with genetic defects.

In a preferred embodiment, the mutant, protein, and/or composition of the present invention are used in combination with an additional therapeutic agent for the treatment of diseases or conditions mediated by pathogenic IgG antibodies.

The present invention also provides a method of administering the pharmaceutical combination to a subject to treat or prevent a gene deficiency-related disease, cancer or infection or a pathogenic IgG antibody-mediated disease or disorder. The method results in a reduction of 20-50%, 50-75%, 75-90%, 90-95%, or 95%, or more than 95% of the antibodies bound by the viral vector; and the method results in a reduction of 20-50%, 50-75%, 75-90%, 90-95%, or 95%, or more than 95% of the pathogenic IgG antibody. Preferably, the drug is for use in a method of treating a gene deficiency-related disease. Preferably, the drug is for use in a method of treating cancer, preventing cancer, and preventing infection. The infection is preferably a viral infection, a bacterial infection, or a fungal infection. Preferably, the drug is for use in a method of treatment of cancer. Preferably, the drug is for use in a method of treating a pathogenic IgG antibody-mediated disease or disorder.

Preferably, the additional therapeutic agent is a viral vector drug; preferably, the viral vector drug is an oncolytic virus, a viral vaccine, or a gene therapy virus.

Preferably, the additional therapeutic agent is an antibody.

Preferably, the additional therapeutic agent is a polypeptide drug capable of reducing the level of blood IgG, such as Efgartigimod. More preferably, the polypeptide drug capable of reducing the level of blood IgG is used in the treatment of the above-mentioned pathogenic IgG antibody-mediated disease.

Preferably, the components of the pharmaceutical combination are administered separately or the components of the pharmaceutical combination are administered simultaneously.

In these uses and methods as described above, an additional therapeutic agent, such as an anti-inflammatory agent can be further combined.

In some embodiments, the additional therapeutic agent is a leukocyte depleting agent.

In some embodiments, the additional therapeutic agent is a B-cell depleting agent.

In some embodiments, the B-cell depleting agent is an antibody, preferably an antibody for tumor therapy, more preferably the antibody specifically binds to CD10, CD19, CD20, CD21, CD22, CD23, CD24, CD37, CD53, CD70, CD72, CD74, CD75, CD77, CD79a, CD79b, CD80, CD81, CD82, CD83, CD84, CD3, CD11a, CD14, CD25, CD28, CD30, CD33, CD36, CD38, CD40, CD44, CD52, CD55, CD59, CD56, CD103, CD134, CD137, CD138, CD152, CD3, IL-1B, IL-2R, IL-6, IL-6R, IL-12, IL-23, C5, BAFF, BLyS, BCMA, CXCR-4, ICAM-1, SLAMF7/CS1, TNFa, IgE, CD85, or CD86.

In some embodiments, the additional therapeutic agent is Rituximab, Daclizumab, Basilixumab, Muromonab-CD3, Infliximab, Adalimumab, Omalizumab, Efalizumab, Natalizumab, Tocilizumab, Eculizumab, Golimumab, Canakinumab, Ustekinumab, Belimumab, Daretuzumab, Isatuximab, or a combination thereof.

In some embodiments, the Fc-containing agent is a therapeutic or diagnostic agent, preferably the Fc-containing agent is an antibody, Fc fusion protein antibody drug conjugate.

V. Definitions

Unless defined otherwise, all technical and scientific terms used herein have the same meaning as is commonly understood by one of skill in the art to which this invention belongs. Although any methods, devices, and materials similar or equivalent to those described herein may be used in the practice or testing of the present invention, preferred methods, devices, and materials are now described.

The term "nucleotide" or "polynucleotide" means deoxyribonucleotides, deoxyribonucleosides, ribonucleosides, or ribonucleotides and polymers thereof in single or double stranded form. Unless specifically limited, the term encompasses nucleic acids containing known analogs of naturally occurring nucleotides that have binding properties similar to a reference nucleic acid and are metabolized in a manner similar to naturally occurring nucleotides. Unless otherwise specifically limited, the term also refers to oligonucleotide analogs including PNA (peptide nucleic acids), DNA analogs used in antisense technology (phosphorothioates, phosphoramidates, etc.). Unless otherwise specified, a particular nucleic acid sequence also implicitly encompasses conservatively modified variants thereof (including, but not limited to, degenerate codon substitutions) and complementary sequences, as well as explicitly specified sequences. In particular, degenerate codon substitutions may be achieved by generating sequences in which position 3 of one or more selected (or all) codons are substituted with mixed bases and/or deoxyinosine residues (Batzer et al., Nucleic Acid Res. 19:5081 (1991); Ohtsuka et al., J. Biol. Chem.260: 2605-2608 (1985); and Mol Cell. Probes8: 91-98 (1994)).

The terms "peptide" and "protein" are used interchangeably herein to refer to polymers of amino acid residues. That is, the recitation of a polypeptide is equally applicable to the recitation of a peptide and the recitation of a protein, and vice versa. The terms apply to naturally occurring amino acid polymers as well as to amino acid polymers in which one or more amino acid residues are non-naturally encoded amino acids. As used herein, the term encompasses amino acid chains of any length, including full-length proteins (i.e. antigens) in which amino acid residues are linked via covalent peptide bonds.

The term "host cell" means a cell comprising a nucleotide of the present invention, regardless of the method used for insertion to produce a recombinant host cell, such as direct uptake, transduction, pairing, or other methods known in the art. The exogenous polynucleotide may be maintained as a non-integrating vector, such as a plasmid, or may be integrated into the host genome. The host cell may be a prokaryotic cell or an eukaryotic cell.

The term "transformation" means a method of introducing a heterologous DNA sequence into a host cell or organism.

The term "expression" means transcription and/or translation of an endogenous gene or transgene in a cell.

The positive effect of the present invention is that the present invention provides the use of an immunoglobulin degrading enzyme mutant, wherein the mutant of the present invention has the advantages of high activity, low pre-existing antibodies and high safety when used in the field.

DETAILED DESCRIPTION

The invention is further illustrated by way of the following examples, without thereby limiting the present invention to the scope of the described examples. The experimental methods in the following examples that do not specify specific conditions shall be selected according to conventional methods and conditions, or according to the product manual.

Example 1. Design and Expression of Mutant Library

A wild-type IdeE protein sequence mutation library was designed and constructed to obtain 40 mutant strains through screening.

A polynucleotide sequence encoding the wild-type IdeE protein sequence (SEQ ID NO: 2) was synthesized by codon optimization and added with an N-terminal signal peptide sequence and a C-terminal 6 x histidine tag. The sequence was synthesized and inserted into the pET 32a expression vector. A recombinant plasmid for expressing wild-type IdeE was obtained after correct sequencing. Based on the expression plasmid of wild-type IdeE, the degenerate primer was designed to amplify the original wild-type sequence, and the amplified sequence was inserted into the vector to obtain the recombinant plasmid of the mutant library. The wild-type and mutant library recombinant plasmids were electrotransformed into E. coli BL21 Star (DE3) and plated on an LB agarose plate containing 100 µg/ml ampicillin. Incubation was performed overnight at 37° C. until colonies grew out. Individual colonies were picked and grown overnight in 200 ul of LB medium containing 100 µg/ml ampicillin at 37° C. under 250 rpm. The overnight culture was inoculated into 1 ml of LB medium containing 100 µg/ml ampicillin, and incubated at 37° C. for 4 h, then 0.1 mM IPTG was added, and the incubation was continued overnight at 30° C. Overnight cultures were centrifuged to collect the supernatant. The concentration of mutant protein in the mutant expression supernatant was evaluated by SDS-PAGE.

Example 2. Evaluation of Cleavage Activity of Mutant Against Human IgG1

An ELSIA-based activity assay was established to evaluate the cleavage activity of each mutant against human IgG1. The principle of the assay is to coat a plate with human IgG1 specific antigen and then incubate a sample of supernatant containing a comparable concentration of mutant protein with human IgG1 in a well. The amount of intact or incompletely cleaved human IgG1 bound to the well can be measured using a human IgG1 detection antibody specific for the Fc portion of the antibody. At the same concentration of mutant protein in a given supernatant in a well, the higher the activity of the mutant protein for cleaving human IgG1, the less intact human IgG1 antibody binds to the well, resulting in a lower signal. With the relationship between different concentrations of IgG1 and the corresponding detection signal, an IgG1 standard curve can be made, and the amount of completely cleaved IgG1 can be calculated according to the standard curve by calculating the amount of completely cleaved IgG1. Mutant activity can be assessed as the ratio of completely cleaved IgG1 to the original IgG1.

In order to bring the concentration of the mutant protein in the supernatant harvested in Example 1 to a comparable level, SDS-PAGE detection was performed at the same amount of loading, and the optical density value of the target protein band in the electropherogram was analyzed using Quantity One. In the case of the same amount of loading, the higher the optical density value of the target protein band in the map, the higher the concentration. With the IdeE supernatant as a control, other mutant supernatants were concentrated or diluted, so that the optical density values of mutant protein bands were consistent with those of IdeE control.

Following adjusting the protein concentration in the supernatant to a comparable level, the ELISA assay was performed as follows: the ELISA plate was coated with 2 µg/ml human IgG1 (Trastuzumab) specific antigen (Cat. No. QRE-104, Ruian Biology) at 2-8° C. overnight, and then washed with PBST (PBS+0.05% Tween 20). The washed ELISA plate was blocked with 2% BSA (prepared by PBS) at 37° C. for 2 h and then washed with PBST after blocking.

Preparation of the standard curve: 200 ng/ml Trastuzumab was diluted in gradient with a reaction buffer (10 mM PB, 10 mM NaCl, pH6.5) in a ratio of 1:2 till to 3.125 ng/ml and 100 ul of Trastuzumab with different concentrations were added to the wells of the ELISA plate for substrate (Trastuzumab) standard curve preparation.

Cleavage reaction: the supernatant with the protein concentration being adjusted was diluted 5-fold with the reaction buffer (10 mM PB, 10 mM NaCl, pH6.5), and 50 ul of 100 ng/ml Trastuzumab and 50 ul of the diluted supernatant were added to the wells of the ELISA plate.

The plate was incubated with shaking at 37° C. for 1 h and washed with PBST. Then, 40 ng/ml Goat anti-Human IgG Fc Cross-Adsorbed Secondary Antibody-HRP (Cat. 31413, Thermo) was added to the plate, incubated with shaking at 37° C. for 1 h, and washed with PBST. Then, the plate was incubated with TMB as a chromogenic substrate for HRP for 15 min and terminated with 2N $H_2SO_4$. The absorbance was measured at 450 nm using an enzyme-linked immunosorbent assay (ELISA) reader. The activity of different mutants was evaluated by calculating the concentration of intact or incompletely cleaved Trastuzumab in different test wells from the substrate standard curve and then calculating the proportion of completely cleaved Trastuzumab to the initial Trastuzumab.

The fold relationship of each mutant activity relative to wild-type IdeE activity is shown in Table 1. 40 Mutants screened in Example 1 all had greater than or equal activity to wild-type IdeE, with 15 mutants having 2-fold or greater activity than wild-type IdeE.

TABLE 1

Fold relationship of mutant activity relative
to wild-type IdeE as measured by ELISA.

| Mutant | Fold of activity relative to wild-type | SEQ ID NO: |
|---|---|---|
| T8D | 2.21 | 3 |
| T8E | 2.09 | 4 |
| T8W | 2.58 | 5 |
| T8Y | 2.30 | 6 |
| A10K | 1.99 | 7 |
| A10R | 2.20 | 8 |
| T24A | 2.23 | 9 |
| T24G | 2.09 | 10 |
| T24S | 2.18 | 11 |
| A59I | 2.31 | 12 |
| A59L | 2.41 | 13 |
| A59V | 2.68 | 14 |
| E97D | 2.00 | 15 |
| R280H | 2.30 | 16 |
| R280K | 2.20 | 17 |

Example 3. Evaluation of Thermal Stability of Mutants

From the 15 mutants shown in Table 1, having 2-fold or greater activity than that of wild-type IdeE, 12 mutants were selected to examine their thermal stability. Detection method: the activity detection method is as follows:

The supernatant of wild-type or each mutant was divided into two portions and incubated at 4° C. and 50° C. for 1 h, respectively. After incubation, the activity of wild-type or each mutant was detected according to the ELISA method in Example 2. The percentage (%) of remaining activity of the wild-type or each mutant after incubation at 50° C. for 1 h was calculated using the activity after incubation at 50° C./the activity after incubation at 4° C., thereby comparing the thermostabilities of the wild-type and each mutant.

The fold relationship of mutant activity relative to the wild-type IdeE thermal stability is shown in Table 2. Table 2 shows that 12 mutants all have higher thermal stability than the wild-type, with 7 mutants having 3-fold or greater thermal stability than the wild-type.

TABLE 2

Fold relationship of thermal stability
of mutants relative to wild-type IdeE

| Mutant | Fold of thermal stability relative to wild-type | SEQ ID NO: |
|---|---|---|
| T8D | 4.14 | 3 |
| T8W | 4.43 | 5 |
| T24A | 4.50 | 9 |
| A59L | 3.83 | 13 |
| A59V | 5.20 | 14 |
| E97D | 4.27 | 15 |
| R280H | 4.36 | 16 |

Example 4. Comparison of Activity of Single-Point Mutant for Cleaving Human IgG1

Seven single-point mutants, T8D, T8W, T24A, A59L, A59V, E97D, and R280H, as shown in Table 1 and Table 2, "having 2-fold or greater activity than wild-type IdeE and 3-fold or greater thermal stability than the wild-type" were tested for their activities for cleaving human IgG1.

1. Expression and Purification of Mutants

One single colony from each of the transformed plates of the 5 single-point mutants described above in Example 1 was inoculated into 3 ml of LB medium containing 100 ug/ml ampicillin and incubated overnight at 37° C. under 250 rpm. The overnight culture was inoculated into 50 ml of LB medium containing 100 ug/ml ampicillin, and cultured at 37° C. until the OD600 reached 0.4-0.6. 0.1 mM IPTG was added, and the culture was continued at 30° C. overnight. Overnight cultures were centrifuged to collect the supernatant. The supernatant was then purified using IDA-Ni agarose magnetic beads, and the purified protein was resuspended in PBS buffer using an ultrafiltration centrifuge tube. SDS-PAGE was used to evaluate the purity of the purified mutant protein. The OD280 was measured and the purified mutant protein concentration was calculated based on the extinction coefficient.

2. Comparison of Activity of Mutant for Cleaving Human IgG1

To further evaluate the activity of different mutants for cleaving human IgG1 relative to the wild-type IdeE, SDS-PAGE was used to show the different concentrations of cleavage products resulting from each mutant on human IgG1. Purified mutant or wild-type IdeE was diluted to 0.002 mg/mL and 0.001 mg/mL, respectively. 50 ul of mutant or wild-type IdeE with different concentrations were taken and added into 50 ul of reaction system containing 2 mg/ml Trastuzumab to start the cleavage reaction. The reaction system was placed at 37° C. for 30 min. The samples were mixed with an equal volume of 2 x SDS loading buffer and placed in a 75° C. water bath for 5 min. The cleavage products were detected by SDS-PAGE.

Figure 2:
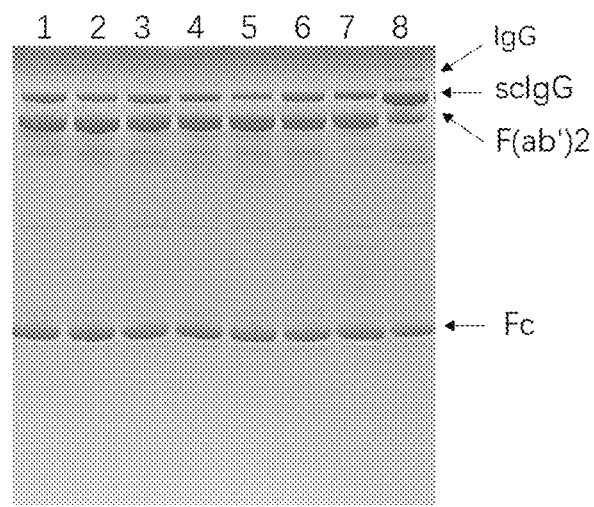
FIG. 2 shows a SDS-PAGE gel electropherogram of the cleavage products resulting from digesting human IgG1 by 7 single-point mutants and wild-type IdeE (enzyme: substrate=1:2000).

FIG. 1 shows the electropherogram of the cleavage products resulting from cleaving human IgG1 by 7 single-point mutants and wild-type IdeE (enzyme: substrate=1:1000). FIG. 2 shows the electropherogram of the cleavage products resulting from cleaving human IgG1 by 7 single-point mutants and wild-type IdeE (enzyme: substrate=1:2000). None of the 7 single-point mutants cleaved IgG1 at a concentration of 0.001 mg/ml less than 0.002 mg/ml wild-type IdeE, indicating that the seven single-point mutants cleaved human IgG1 no less than 2 folds as active as wild-type IdeE.

Example 5. Comparison of Activity and Thermal Stability of N-Terminal Truncated Truncation Mutant for Cleaving Human IgG1

Five N-terminal truncated mutants were constructed by deleting the first 15 N-terminal amino acids (D1-V15), the first 16 N-terminal amino acids (D1-P16), the first 17 N-terminal amino acids (D1-H17), the first 18 N-terminal amino acids (D1-Q18), and the first 19 N-terminal amino acids (D1-I19) from wild-type IdeE (see Table 3).

TABLE 3

Truncated mutant Sequence Design

| Mutant | Modification relative to wild-type or mutant sequence | SEQ ID NO: |
|---|---|---|
| WT_del15 | Deleting the first 15 amino acids of SEQ ID NO: 2 | 18 |
| WT_del16 | Deleting the first 16 amino acids of SEQ ID NO: 2 | 19 |
| WT_del17 | Deleting the first 17 amino acids of SEQ ID NO: 2 | 20 |
| WT_del18 | Deleting the first 18 amino acids of SEQ ID NO: 2 | 21 |
| WT_del19 | Deleting the first 19 amino acids of SEQ ID NO: 2 | 22 |

1. Expression and Purification of Mutants

The mutant polynucleotide sequences in Table 3 were synthesized according to the method of Example 1, and a mutant expression recombinant plasmid was constructed and transformed into *E. coli* BL21 Star (DE3). The mutant purified protein was prepared as in Example 4.

2. Comparison of Activity of Mutant for Cleaving Human IgG1

The purified mutant or wild-type IdeE was diluted to 0.002 mg/mL, respectively. 50 ul of diluted mutant or wild-type IdeE were taken and added into 50 ul of reaction system containing 2 mg/ml Trastuzumab to start the cleavage reaction. The reaction system was placed at 37° C. for 30 min. The samples were mixed with an equal volume of 2 x SDS loading buffer and placed in a 75° C. water bath for 5 min. The cleavage products were detected by SDS-PAGE.

Figure 3:
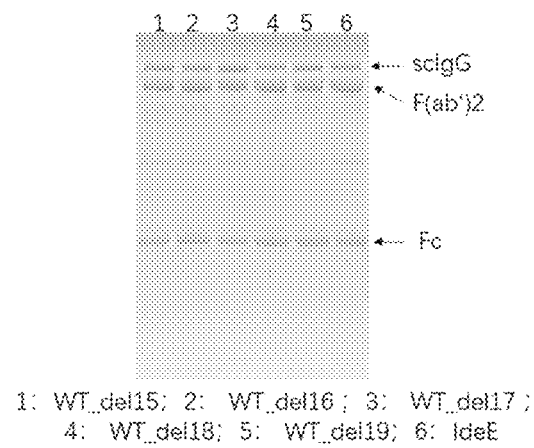
FIG. 3 shows a SDS-PAGE gel electropherogram of the cleavage products resulting from digesting human IgG1 by 5 N-terminal truncated mutants (enzyme: substrate=1:1000).

FIG. 3 shows the electropherogram of the cleavage products resulting from cleaving human IgG1 by 5 truncated mutants (enzyme: substrate=1:1000). The cleavage activities of all five truncated mutants were not significantly different from wild-type IdeE.

3. Evaluation of Thermal Stability of Mutants

The purified mutant or wild-type IdeE was diluted to 0.1 mg/ml, incubated at 50° C. for 1 h, and then diluted to 0.002 mg/ml after incubation. 50 ul of diluted mutant or wild-type IdeE were taken and added into 50 ul of reaction system containing 2 mg/ml Trastuzumab to start the cleavage reaction. The reaction system was placed at 37° C. for 30 min. The samples were mixed with an equal volume of 2 x SDS loading buffer and placed in a 75° C. water bath for 5 min. The cleavage products were detected by SDS-PAGE.

Figure 4:
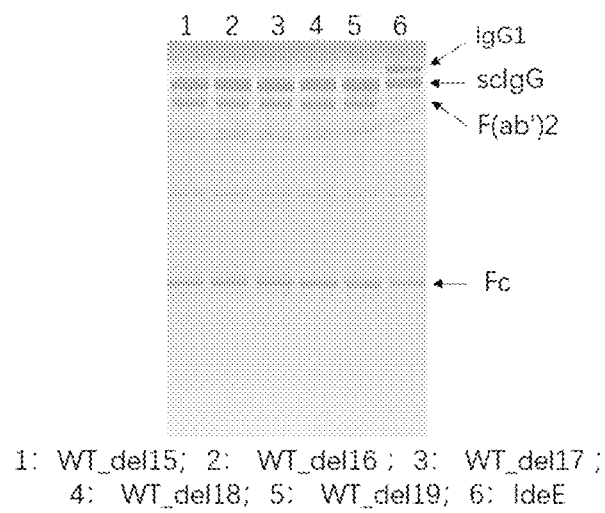
FIG. 4 shows a SDS-PAGE gel electropherogram of the cleavage products resulting from digesting human IgG1 by 5 N-terminal truncated mutants and wild-type IdeE after 1 h of incubation at 50° C. (enzyme: substrate=1:1000).

FIG. 4 shows the electropherogram of the cleavage products resulting from cleaving human IgG1 by 5 truncated mutants and wild-type IdeE after 1 h of incubation at 50° C. (enzyme: substrate=1:1000). The residual activities of the five truncated mutants after heat treatment at 50° C. were significantly higher than or equal to the wild-type, indicating that the thermal stability of the five truncated mutants was significantly improved compared to the wild-type.

Example 6. Comparison of Activity of C-Terminal Truncated Truncation Mutant for Cleaving Human IgG1

Two C-terminal truncated mutants were constructed by deleting the last 5 C-terminal amino acids (W311-S315) and the last 10 C-terminal amino acids (S306-S315), respectively, from wild-type IdeE (see Table 4).

TABLE 4

Truncated mutant Sequence Design

| Mutant | Modification relative to wild-type or mutant sequence | SEQ ID NO: |
|---|---|---|
| WT_delC5 | Deleting the last 5 amino acids of SEQ ID NO: 2 | 23 |
| WT_delC10 | Deleting the last 10 amino acids of SEQ ID NO: 2 | 24 |

1. Expression and Purification of Mutants

The mutant polynucleotide sequences in Table 4 were synthesized according to the method of Example 1, and a mutant expression recombinant plasmid was constructed and transformed into *E. coli* BL21 Star (DE3). The mutant purified protein was prepared as in Example 4.

2. Comparison of Activity of Mutant for Cleaving Human IgG1

The purified mutant or wild-type IdeE was diluted to 0.002 mg/mL, respectively. 50 ul of diluted mutant or wild-type IdeE were taken and added into 50 ul of reaction system containing 2 mg/ml Trastuzumab to start the cleavage reaction. The reaction system was placed at 37° C. for 30 min. The samples were mixed with an equal volume of 2 x SDS loading buffer and placed in a 75° C. water bath for 5 min. The cleavage products were detected by SDS-PAGE.

Figure 5:
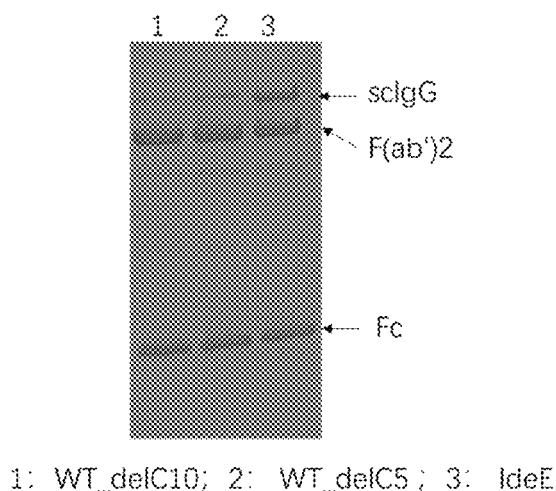
FIG. 5 shows a SDS-PAGE gel electropherogram of the cleavage products resulting from digesting human IgG1 by 2 C-terminal truncated mutants (enzyme: substrate=1:1000).

FIG. 5 shows the electropherogram of the cleavage products resulting from cleaving human IgG1 by two C-terminal truncated mutants (enzyme: substrate=1:1000). Both truncated mutants had more than 2-fold higher cleavage activity than wild-type IdeE.

Example 7. Comparison of Activity and Thermal Stability of the Combined Mutant for Cleaving Human IgG1

Based on the 5 single-point mutants of T24A, A59L, A59V, E97D, and R280H, the first 18 (D1-Q18) amino acids were deleted respectively, and 5 combined mutants were constructed (see Table 5).

3. Evaluation of Thermal Stability of Mutants

The purified mutants were diluted to 0.1 mg/ml, incubated at 50° C. for 1 h, and then diluted to 0.001 mg/ml after incubation. 50 ul of diluted mutant or wild-type IdeE were taken and added into 50 ul of reaction system containing 2 mg/ml Trastuzumab to start the cleavage reaction. The reaction system was placed at 37° C. for 30 min. The samples were mixed with an equal volume of 2 x SDS loading buffer and placed in a 75° C. water bath for 5 min. The cleavage products were detected by SDS-PAGE.

Figure 6:
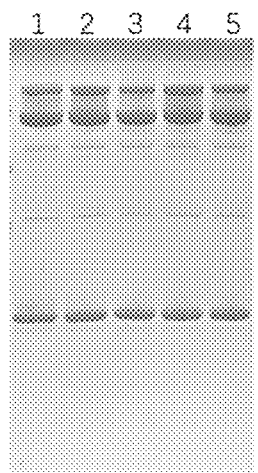
FIG. 6 shows a SDS-PAGE gel electropherogram of the cleavage products resulting from digesting human IgG1 by 5 mutants with mutation combinations (enzyme: substrate=1:2000).
Figure 7:
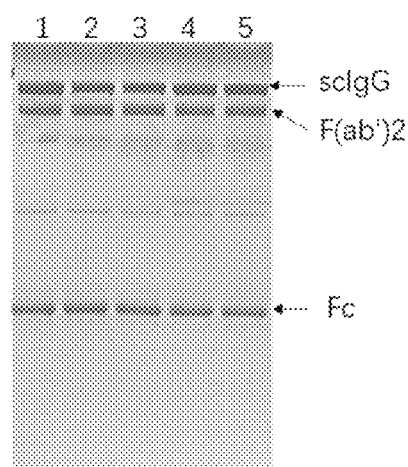
FIG. 7 shows a SDS-PAGE gel electropherogram of the cleavage products resulting from digesting human IgG1 by 5 mutants with mutation combinations after 1 h of incubation at 50° C. (enzyme: substrate=1:2000).

FIG. 7 shows the electropherogram of the cleavage products resulting from cleaving human IgG1 by 5 combined mutants after 1 h of incubation at 50° C. (enzyme: substrate=1:2000). Comparing the cleavage effects of FIG. 6 and FIG. 7, the 5 combined mutants showed only a slight decrease in activity after heat treatment at 50° C., indicating that the 5 combined mutants also showed a significant increase in thermal stability relative to the wild-type.

Example 8. Comparison of the Activity of the E97D Del18 Mutant with IdeS and IdeZ The E97D_del18 mutant purified in Example 7 was serially diluted to 20 ug/mL, 10 ug/mL, 5 ug/mL, 2.5 ug/mL, and 1.25 ug/mL. Ides (FabRICATOR®, Cat. A0-FRI-020, Genovis) was diluted to 2 U/ul, 1 U/ul, 0.5 U/ul, 0.25 U/ul, and 0.125 U/ul, respectively, as indicated. Idez (FabRICATOR-Z®, Cat. A0-FRZ-020, Genovis) to 0.4 U/ul, 0.2 U/ul, 0.1 U/ul, 0.05 U/ul, and 0.025 U/ul, respectively. 50 ul of mutants, IdeS or IdeZ at different concentrations were taken, respectively, added with 50 ul of the reaction system con-

TABLE 5

Combined Mutant Sequence Design

| Mutant | Modification relative to wild-type or mutant sequence | SEQ ID NO: |
|---|---|---|
| T24A_del18 | Deleting the first 18 amino acids of SEQ ID NO: 9 | 25 |
| A59L_del18 | Deleting the first 18 amino acids of SEQ ID NO: 13 | 26 |
| A59V_del18 | Deleting the first 18 amino acids of SEQ ID NO: 14 | 27 |
| E97D_del18 | Deleting the first 18 amino acids of SEQ ID NO: 15 | 28 |
| R280H_del18 | Deleting the first 18 amino acids of SEQ ID NO: 16 | 29 |

1. Expression and Purification of Mutants

The mutant polynucleotide sequences in Table 5 were synthesized according to the method of Example 1, and a mutant expression recombinant plasmid was constructed and transformed into *E. coli* BL21 Star (DE3). The mutant purified protein was prepared as in Example 4.

2. Comparison of Activity of Mutant for Cleaving Human IgG1

The purified mutants were diluted to 0.001 mg/mL, respectively. 50 ul of diluted mutant or wild-type IdeE were taken and added into 50 ul of reaction system containing 2 mg/ml Trastuzumab to start the cleavage reaction. The reaction system was placed at 37° C. for 30 min. The samples were mixed with an equal volume of 2 x SDS loading buffer and placed in a 75° C. water bath for 5 min. The cleavage products were detected by SDS-PAGE.

FIG. 6 shows the electropherogram of the cleavage products resulting from cleaving human IgG1 by 5 combined mutants (enzyme: substrate=1:2000). Comparing the cleavage effects of FIG. 6 and FIG. 2, there was no significant difference in cleavage activity between the 5 truncated mutants and the single-point combined mutant, indicating that the combined mutant also has no less than 2-fold activity for cleaving human IgGl that of the wild-type IdeE.

taining 2 mg/ml Trastuzumab to start the cleavage reaction. The reaction system was placed at 37° C. for 30 min. The samples were mixed with an equal volume of 2 x SDS loading buffer and placed in a 75° C. water bath for 5 min. The cleavage products were detected by SDS-PAGE.

Figure 8:
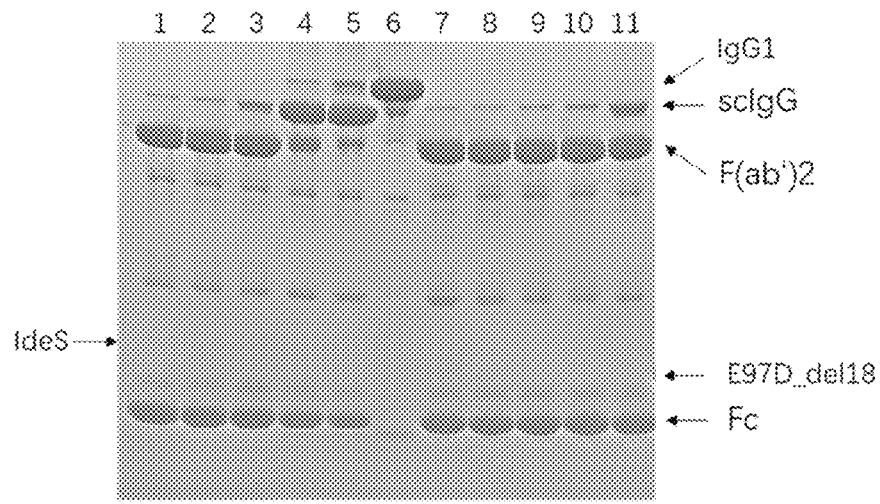
FIG. 8 shows a SDS-PAGE gel electropherogram of the cleavage products resulting from digesting human IgG1 by the E97D_del18 mutant and IdeS at various concentrations.

FIG. 8 shows the electropherogram of the cleavage products resulting from cleaving human IgG1 by E97D_del18 mutant and IdeS at different concentrations. From the enzyme protein bands on the electropherogram, it can be determined that the IdeS enzyme concentration in lane 1 is between the E97D_del18 mutant enzyme concentration in lanes 7 and 8, and thus recursively the IdeS enzyme concentration in lane 3 is between the E97D_del18 mutant enzyme concentrations in lanes 9 and 10, while the enzymatic cleavage effect of IgG1 in lane 3 is between lanes 10 and 11, and thus it can be inferred that the activity of the E97D_del18 mutant for cleaving human IgG1 is nearly twice that of IdeS.

Figure 9:
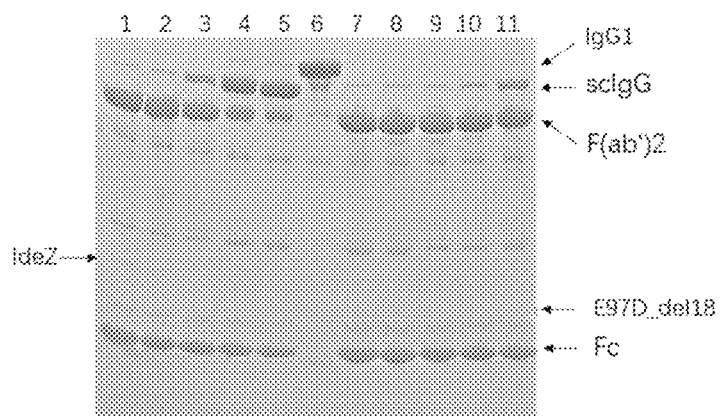
FIG. 9 shows a SDS-PAGE gel electropherogram of the cleavage products resulting from digesting human IgG1 by the E97D_del18 mutant and IdeZ at various concentrations.

FIG. 9 shows the electropherogram of the cleavage products resulting from cleaving human IgG1 by E97D_del18 mutant and IdeZ at different concentrations. From the enzyme protein bands on the electropherogram, it can be determined that the IdeZ enzyme concentration in lane 1 is higher than the E97D_del18 mutant enzyme concentration in lane 7, and thus recursively the IdeZ enzyme concentration in lane 3 is higher than the E97D_del18 mutant enzyme concentration in lane 9, i.e. higher than 4 times the E97D_del18 mutant enzyme concentration in lane 11, while the enzymatic cleavage effect of IgG1 in lane 3 is close to that in lane 11, and thus it can be inferred that the activity of the E97D_del18 mutant for cleaving human IgGI is higher than 4 times that of IdeZ.

Example 9. In Vitro Assay of the Activity of E97D Del18 Mutant for Cleaving Human IgG1

The in vitro cleavage activity of the E97D_del18 mutant on human IgGI was evaluated by measuring the amount of intact or single-cleaved IVIg added to the serum or plasma of mouse treated with the E97D_del18 mutant and human IVIg. Different groups of mouse serum or plasma enzymatic cleavage systems were prepared according to Table 6.

TABLE 6

Mouse Serum or Plasma Enzymatic Cleavage System

| Grouping name | PBS volume (μl) | Serum or plasma volume (μl) | IVIg concentration in the system (mg/ml) | E97D_del18 concentration in the system (mg/ml) | Iodoacetic acid concentration in the system (mM) |
|---|---|---|---|---|---|
| IVIg control | 100 | / | 10 | / | / |
| Mouse serum control group | / | 100 | 10 | / | / |
| Normal mouse serum enzymatic cleavage group | / | 100 | 10 | 0.05 | / |
| Mouse serum iodoacetate treated group | / | 100 | 10 | 0.05 | 2 |
| Mouse serum control group | / | 100 | 10 | / | / |
| Normal mouse plasma enzymatic cleavage group | / | 100 | 10 | 0.05 | / |
| Mouse plasma iodoacetic acid treated group | / | 100 | 10 | 0.05 | 2 |

The effect of iodoacetic acid in the iodoacetic acid treated group was to inhibit the activity of the IgG degrading enzyme.

The system was placed at 37° C. for 30 min. 20 ul of sample was taken and mixed with the same volume of 2 x SDS non-reduction loading buffer, and placed in a 75° C. water bath for 5 min. The cleavage product was detected by using SDS-PAGE.

FIG. 10 shows an electropherogram of the cleavage product resulting from cleaving human IVIg by the E97D_del18 mutant in mouse serum and plasma. The results show that E97D_del18 is effective in cleaving human IVIg in both mouse serum and plasma.

The in vitro cleavage activity of the E97D_del18 mutant against human IgG1 was evaluated by adding mouse or human serum treated with the E97D_del18 mutant. Different groups of mouse or human serum enzymatic cleavage systems were prepared according to Table 7.

TABLE 7

Mouse or Human Serum Enzymatic Cleavage Systems

| Grouping name | Mouse serum volume (μl) | Normal human serum volume (μl) | Concentration of E97D_del18 in the system (mg/ml) |
|---|---|---|---|
| Mouse serum control group | 100 | / | / |
| Mouse serum enzymatic cleavage group | 100 | / | / |

TABLE 7-continued

Mouse or Human Serum Enzymatic Cleavage Systems

| Grouping name | Mouse serum volume (μl) | Normal human serum volume (μl) | Concentration of E97D_del18 in the system (mg/ml) |
|---|---|---|---|
| Human serum control group | / | 100 | 0.02 |
| Human serum enzymatic cleavage group | / | 100 | 0.02 |

The system was left to react at 37° C. for 24 h. 20 ul of sample was taken, mixed with the same volume of 2 x SDS reducing loading buffer, diluted with 1 x SDS reducing loading buffer by 20 times, and placed at a 75° C. water bath for 5 min. The cleavage product was detected by using SDS-PAGE.

FIG. 11 shows the electropherograms of the cleavage products of the E97D_del18 mutant in mouse and human serums. The results show that E97D_del18 cleaves in human serum to produce an apparent 25 kD Fc fragment, but not in mouse serum, indicating that E97D_del18 is effective in specifically cleaving IgG1 in human serum with little or no cleavage activity against IgG1 in mouse serum.

Example 10. E97D Del18 Mutant Cleaves Immunoglobulins of Different Species

The in vitro cleavage activity of the E97D_del18 mutant against serum immunoglobulins from animals of different species was evaluated by measuring the amount of intact or single-cleaved IgG added to the E97D_del18 mutant and serum or plasma from animals of different species. Different species of serum or antibody enzymatic cleavage system were prepared according to Table 8 and Table 9.

TABLE 8

Beagle dog serum and antibody enzymatic cleavage systems of different species

| Grouping name | Immunoglobulin concentration in the system (mg/ml) | Concentration of E97D_del18 in the system (mg/ml) |
|---|---|---|
| Beagle dog serum control group | 10 | / |
| Beagle dog serum enzymatic cleavage group | 10 | 0.025/1 |
| Rabbit polyclonal IgG antibody 1 control group | 1 | / |
| Rabbit polyclonal IgG antibody 1 control group | 1 | 0.005 |
| Rabbit polyclonal IgG antibody 2 control group | 1 | / |
| Rabbit polyclonal IgG antibody 2 control group | 1 | 0.005 |
| Mouse monoclonal antibody IgG1 control group | 1 | 0.005 |
| Mouse monoclonal antibody IgG1 enzymatic cleavage | 1 | 0.005 |
| Mouse monoclonal antibody IgG2a control group | 1 | 0.005 |
| Mouse monoclonal antibody IgG2a enzymatic cleavage group | 1 | 0.005 |

The system was left to react at 37° C. for 1 hour and the enzymatic cleavage products were detected by SDS-PAGE.

TABLE 9

Serum Enzymatic Cleavage Systems of Different Species

| Grouping name | Immunoglobulin concentration in the system (mg/ml) | Concentration of E97D_del18 in the system (mg/ml) |
|---|---|---|
| SD rat serum control group | 5 | / |
| SD rat serum enzymatic cleavage group | 5 | 0.025/0.5 |
| ICR mouse serum control group | 5 | / |
| ICR mouse serum enzymatic cleavage group | 5 | 0.025/0.5 |
| New Zealand rabbit serum control group | 5 | / |
| New Zealand rabbit serum enzymatic cleavage group | 5 | 0.025/0.5 |
| Beagle dog serum control group | 5 | / |
| Beagle dog serum enzymatic cleavage group | 5 | 0.025/0.5 |
| Cynomolgus monkey serum control group | 5 | / |
| Cynomolgus monkey serum enzymatic cleavage group | 5 | 0.025/0.5 |
| Bama miniature pig serum control group | 5 | / |
| Bama miniature serum enzymatic cleavage group | 5 | 0.025/0.5 |

FIGS. 12A-12D show the effect of the E97D_del18 mutant on serums and antibodies from different species. The results showed that E97D_del18 could effectively cleave canine IgG, rabbit IgG and mouse IgG2a, but could not cleave mouse IgG1. E97d_del18 can effectively cleave rabbit, canine, and monkey serum IgG, with the best cleavage effect for rabbit serum IgG, poor cleavage effect for pig serum IgG, and almost no cleavage effect for rat and mouse serum IgG.

Example 11. Low Pre-Existing Antibodies in the Human Body Against the E97D Del18 Mutant The assay is based on competition between the E97D_del18 mutant and IdeS for binding to anti-E97D_del18/IdeS antibodies. Pre-incubation of the test enzyme with human serum will enable the binding of the anti-E97D_del18/IdeS antibody with the E97D_del18 mutant and IdeS.

The E97D_del18 mutant was coated with IdeS on a well plate overnight, then washed with PBST, and blocked in a 2% BSA blocking solution for 1 h. A mixed plate was prepared with step-wise diluted test mutant, IdeS, and human serum. The mixed plate was incubated for 1 hour at room temperature with shaking. After PBST washing, the mixed plated was added with biotinylated E97D_del18 mutant and IdeS, then SA-HRP, developed with TMB and read. Parallel alignment resulted in pre-existing antibodies for E97D_del18 and IdeS in approximately 80 human blood samples.

Results are shown in Table 10. The proportion of pre-existing antibodies in normal human serum was as high as about 90% for IdeS and only about 20% for the E97D_del18 mutant. The E97D_del18 mutant has significantly fewer pre-existing antibodies than IdeS in vivo, demonstrating that the E97D_del18 mutant is less immunogenic and more conducive to in vivo administration.

TABLE 10

Pre-existing antibody alignment of E97D_del18 mutant and IdeS in human blood samples

|  | E97D_del18 mutants | IdeS |
|---|---|---|
| Total number of human blood samples (cases) | 76 | 76 |
| Percentage of pre-existing antibody positive samples (%) | 18.4 | 89.5 |

Example 12. In Vivo Assay of the Activity of E97D Del18 Mutant for Cleaving Human IgG1

Two mouse (two parallel experiments, mouse no. 1 and 2) were injected intraperitoneally with human IVIg (intravenous immunoglobulin) under sterile conditions at a dose of 1 g/kg. 24 hours after the injection of human IVIg, the IgG degrading enzyme mutant (E97D_del18) was injected intravenously into mouse at a dose of 5 mg/kg. Blood samples were collected at 0 h, 15 min, 2 h, 6 h, and 24 h after injection of E97D_del18, and serum samples were collected from both mouse. 20 ul serum sample was taken and mixed with the same volume of 2 x SDS non-reduction loading buffer, and diluted by 1 x SDS non-reduction loading buffer by 20 times. The mixture was placed in a 75° C. water bath for 5 min, and detected by SDS-PAGE.

FIG. 13 shows the electropherogram of the cleavage products resulting from cleaving human IVIg by E97D_del18 in mouse at different times. The results showed that E97D_del18 could cleave IVIg significantly in mouse, and had completely cleaved with 15 min.

Example 13. Comparison of the Activity of
Combined Mutant for Cleaving Human IgG1

On the basis of the above mutants, 6 combined mutants were further constructed, the sequences of which are shown in Table 11.

TABLE 11

Combined mutants

| Mutant | Modification relative to wild-type or mutant sequence | SEQ ID NO: |
|---|---|---|
| E97D_del18_delC5 | Deleting the last 5 amino acids of SEQ ID NO: 28 | 30 |
| E97D_del18_delC10 | Deleting the last 10 amino acids of SEQ ID NO: 28 | 31 |
| A59V_del18_delC5 | Deleting the last 5 amino acids of SEQ ID NO: 27 | 32 |
| A59L_del18_delC5 | Deleting the last 5 amino acids of SEQ ID NO: 26 | 33 |
| R280H_del18_delC5 | Deleting the last 5 amino acids of SEQ ID NO: 29 | 34 |
| E97D_A59V_R280H | E97D, A59V, R280H triple mutant combination | 35 |

1. Expression and Purification of Mutants

The mutant polynucleotide sequences in Table 11 were synthesized according to the method of Example 1, and a mutant expression recombinant plasmid was constructed and transformed into *E. coli* BL21 Star (DE3). The mutant purified protein was prepared as in Example 4.

2. Comparison of Activity of Mutant for Cleaving Human IgG1

The purified mutants were diluted to 0.001 mg/mL, respectively. 50 ul of diluted mutant or wild-type IdeE were taken and added into 50 ul of reaction system containing 2 mg/ml Trastuzumab to start the cleavage reaction. The reaction system was placed at 37° C. for 30 min. The samples were mixed with an equal volume of 2 x SDS loading buffer and placed in a 75° C. water bath for 5 min. The cleavage products were detected by SDS-PAGE.

Figure 14B:

FIGS. 14A and 14B show the electropherogram of the cleavage products resulting from cleaving human IgG1 by the 6 combined mutants (enzyme: substrate=1:2000).

Example 14. Design and Expression of Novel Mutant

Through further analysis and screening of mutation data, IdeE mutant SEQ ID NO: 36 was selected for evaluation, with the code of IdeEv2. After codon optimization, the polynucleotide sequence encoding the mutant was synthesized, and the N-terminal signal peptide sequence was added. After synthesis, the sequence was inserted into pET 32a expression vector. After sequencing, the recombinant plasmid for expression was obtained. The mutant recombinant plasmids were electrotransformed into *E. coli* BL21 Star (DE3) and plated on an LB agarose plate containing 100 ug/ml ampicillin. Incubation was performed overnight at 37° C. until colonies grew out. Individual colonies were picked and grown overnight in 200 ul of LB medium containing 100 ug/ml ampicillin at 37° C. under 250 rpm. The overnight culture was inoculated into 1 ml of LB medium containing 100 ug/ml ampicillin, incubated at 37° C. for 4 h, then 0.1 mM IPTG was added, and the incubation was continued overnight at 30° C. Overnight cultures were centrifuged to collect the supernatant. SDS-PAGE was used to evaluate the expression of the mutant protein in the mutant expression supernatant. The supernatant was purified by ion exchange chromatography followed by hydrophobic chromatography to obtain pure protein. Ides, IdeZ proteins were prepared in the same manner. The purity of the protein was measured to be more than 95% by SEC-HPLC method.

Example 15. Comparison of the Activity and Thermal Stability of the IDEEV2 Mutant for Digesting Human IgG1

1. Comparison of Activity of Mutant for Digesting Human IgG1

Figure 15A:
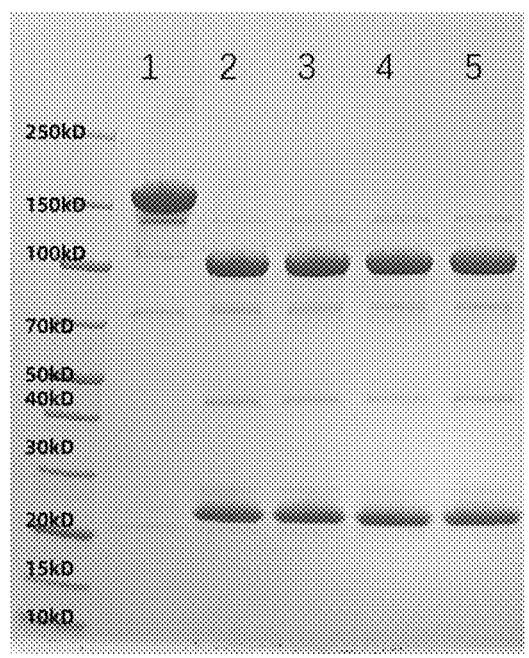
FIG. 15A shows the IDEEV2 activity assay map, wherein lanes 1-5 show un-digested IgG1, and IgG1 digested by IdeZ, IdeS, IdeE, and IDEEV2, respectively (non-reduction electrophoresis).
Figure 15B:
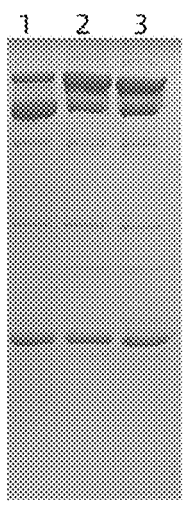
FIG. 15B shows the thermostable biological activity assay map of the IDEEV2 mutant. Lanes 1 to 3 show IgGI digested by IDEEV2, E97D_del18, and IdeE, respectively (non-reduction electrophoresis).

Purified mutant and wild-type IdeE, IdeS, IdeZ were diluted to 0.0025 mg/mL, respectively. 50 ul of mutant, IdeE, IdeS, or IdeZ at different concentrations were added into 50 ul of reaction system containing 2 mg/ml Trastuzumab to start the cleavage reaction. The reaction system was placed at 37° C. for 30 min. The samples were mixed with an equal volume of 2 x SDS loading buffer and placed in a 75° C. water bath for 5 min. The cleavage products were detected by SDS-PAGE. The results showed that the combined mutant can cleave human IgG1 with activity similar to wild-type IdeE (FIG. 15A). 2. Evaluation of thermal stability of mutant The purified mutants were diluted to 0.1 mg/ml, incubated at 50° C. for 1 h, and then diluted to 0.0025 mg/mL after incubation. 50 ul of diluted mutant or wild-type IdeE were taken and added into 50 ul of reaction system containing 2 mg/ml Trastuzumab to start the cleavage reaction. The reaction system was placed at 37° C. for 30 min. The samples were mixed with an equal volume of 2 x SDS loading buffer and placed in a 75° C. water bath for 5 min. The cleavage products were detected by SDS-PAGE. The results showed that the mutant IDEEV2 had the least decrease in activity after heat treatment at 50° C., indicating that the mutant IDEEV2 also has a significant increase in thermal stability compared with the wild-type and other mutants.

Example 16. Evaluation of the Cleavage Specificity of IDEEV2 Mutants Against Different Human Immunoglobulins The cleavage specificity of the IDEEV2 mutants for different substrates was further evaluated by visualizing the cleavage products generated by the mutants on different human IgG on SDS-PAGE. The purified IDEEV2 mutants were diluted to 0.01 mg/mL, respectively. 50 ul of mutant or wild-type IdeE with different concentrations were taken respectively and added into 50 ul of reaction system containing 2 mg/ml different immunoglobulins (human IgG1-4, IgM, IgA, IgE, and IgD) to start the cleavage reaction. The reaction system was placed at 37° C. for 30 min. The samples were mixed with an equal volume of 2 x SDS loading buffer and placed in a 75° C. water bath for 5 min. The cleavage products were detected by SDS-PAGE.

Figure 16A:
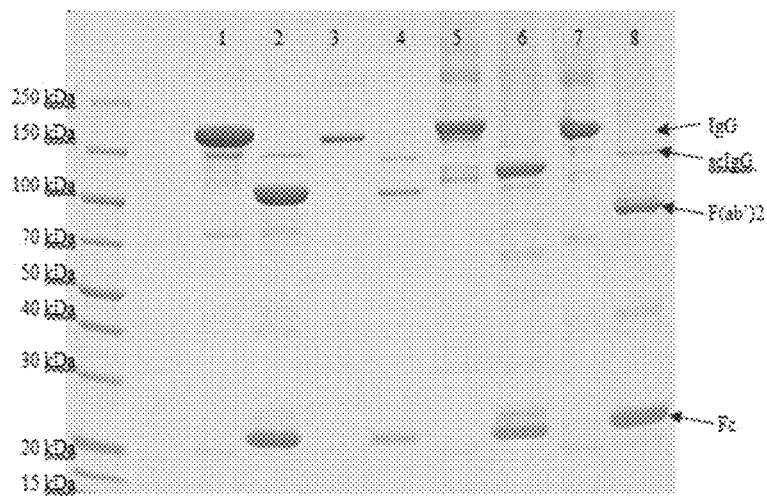
FIG. 16A shows a SDS-PAGE gel electropherogram of the cleavage products resulting from digesting human IgG1-4 by IDEEV2 mutant and IdeS (enzyme: substrate=1:200). Lanes 1-12 show the non-digested control and enzymatic cleavage products with IDEEV2: substrate of 1:200 for IgG1, IgG2, IgG3, and IgG4, respectively (non-reduction electrophoresis).
Figure 16B:
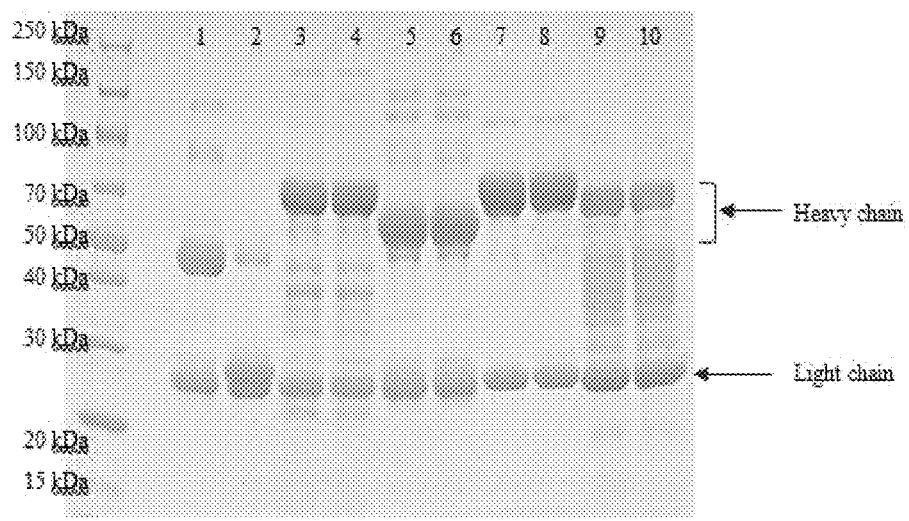
FIG. 16B shows a SDS-PAGE gel electropherogram of the cleavage products resulting from digesting different human immunoglobulins by the IDEEV2 mutant and IdeS (enzyme: substrate=1:200). Lanes 1-12 show un-digested control and enzymatic cleavage products with IDEEV2: substrate of 1:200 for IgG, IgM, IgA, IgE, and IgD, respectively (reduction electrophoresis).

The results show that IDEEV2 can efficiently cleave human IgG1, IgG2, IgG3, and IgG4 (FIG. 16A) and does not cleave human immunoglobulins IgA, IgE, IgD, and IgM (FIG. 16B), indicating that this variant has high substrate specificity.

Example 17. IDEEV2 Mutants Cleave Immunoglobulins of Different Species

The in vitro cleavage activity of IDEEV2 mutants against immunoglobulins of different species was evaluated by measuring the amount of intact or single-cleaved IgG added to the IDEEV2 mutant and serum or plasma from animals of different species. According to the protein ratio of IDEEV2: purified IgG of different animal species or humans=1:200, rabbit, dog, rat, mouse, monkey, and human purified IgG were cleaved at 37° C. for 1 hour, and non-reduction SDS-PAGE electrophoresis was used to detect the digested products.

Figure 17:
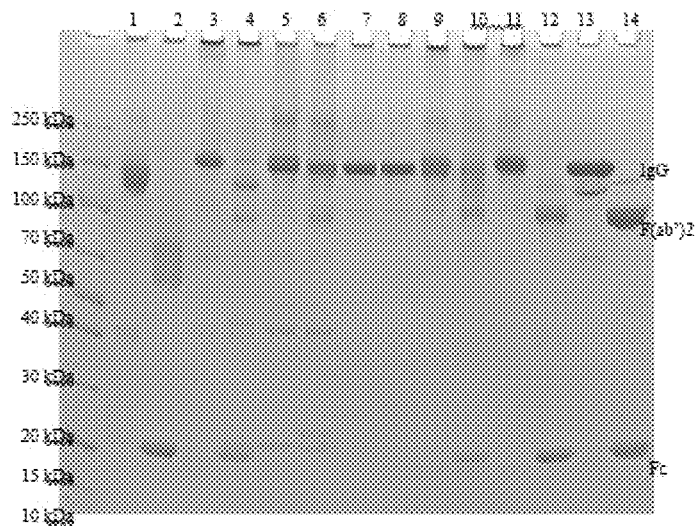
FIG. 17 shows an electropherogram of the cleavage products resulting from digesting purified IgG of different animal species by the IDEEV2 mutant. Lanes 1-12 are un-digested control and enzymatic cleavage products resulting from digesting rabbit IgG, dog IgG, rat IgG, mouse IgG, monkey IgG, human IgG, and human IgG1 with IDEEV2, respectively. (IDEEV2: substrate was 1:200).

The results showed that IDEEV2 can in species-specificity effectively digest IgG in rabbits, dogs, monkeys, and humans, but not in rat and mouse serums (FIG. 17).

Example 18. In Vivo Assay of Digesting New Zealand Rabbit IgG by IDEEV2 Mutant The activity of IDEEV2 for digesting IgG in animals was studied using New Zealand rabbits. IDEEV2 was administered to New Zealand rabbits by intravenous infusion once a week twice at a dose of 2 mg/kg. Blood samples were tested for IgG content in animal serum using ELISA or SDS-PAGE method to evaluate the enzymatic cleavage of IgG by IDEEV2 intravenous infusion in animals.

Figure 18A:
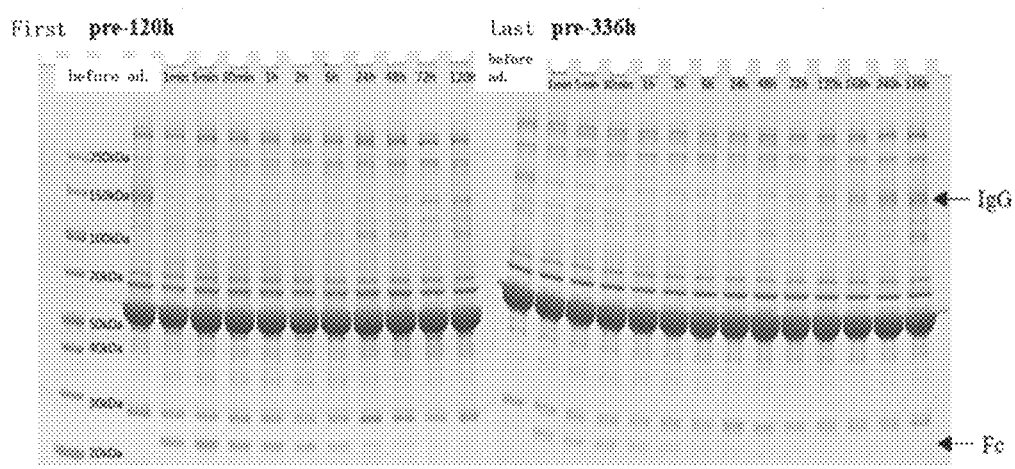
FIG. 18A shows the IgG content as a function of time (SDS-PAGE test results) in New Zealand rabbits injected intravenouslly with IDEEV2 once weekly for twice at a dose of 2 mg/kg.

The results show that IDEEV2 can rapidly cleave IgG in rabbits: at the first blood sample collection point after the first and last administrations (1 min before the end of administration), the IgG content in rabbits at the dose of 2 mg/kg was basically lower than the lower limit of detection. About 1-2 days after the first and last administrations, the IgG level in the rabbit gradually increased, and the content of digested products gradually returned to the pre-dose level. After 2 administrations, the IgG content in the rabbit can return to the normal level range after about 10 days. (FIG. 18A)

Figure 18B:
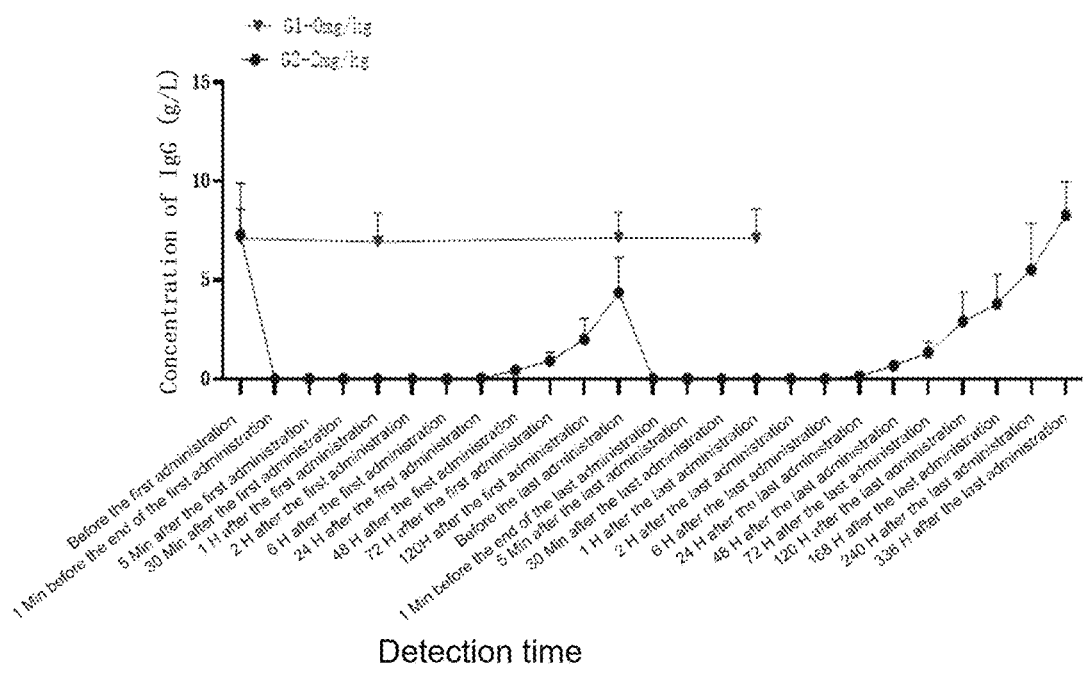
FIG. 18B shows the IgG content as a function of time (ELISA test results) in New Zealand rabbits injected intravenouslly with IDEEV2 once weekly for twice at a dose of 2 mg/kg.

IDEEV2 was administered intravenously to New Zealand rabbits once a week, four times a week. Blood samples from the 0.2, 2, and 20 mg/kg dose groups showed that IDEEV2 can rapidly cleave IgG in rabbits. The lowest dose (0.2 mg/kg) has complete pharmacological activity. (FIG. 18B)

From the above data, it can be seen that after intravenous infusion of IDEEV2 to New Zealand rabbits, IgG in the rabbit body can be rapidly cleaved within a dose range of 0.2-20 mg/kg. Most IgG in the rabbit body was cleaved within the first blood sample collection point (1 min before the end of administration) after IDEEV2 administration. About 1-2 days after administration, the content of the cleaved product gradually returns to the pre-dose level. About 10 days after administration, the IgG content in the rabbit can recover to the normal level range.

Example 19. In Vivo Assay of Digesting Beagle IgG by IDEEV2 Mutant

IDEEV2 was administered intravenously to Beagle dogs once a week, twice a week. Blood sample test results of 0.2, 2, and 20 mg/kg groups showed that IDEEV2 could rapidly cleave IgG in dogs. About 3 days after the first and last administration, the IgG level in dogs gradually increased, and the content of digested products returned to the pre-dose level. After dosing twice, there was a certain individual difference in the increase of IgG in convalescent dogs (2 dogs/gender/group), which could be recovered to the normal level range after about 10 days at doses of 0.2 and 2 mg/kg, and basically recovered to the normal level range after 4 weeks at a dose of 20 mg/kg. The decrease and recovery rate of IgG content showed a dose-effect relationship with the administered dose.

Figure 19A:
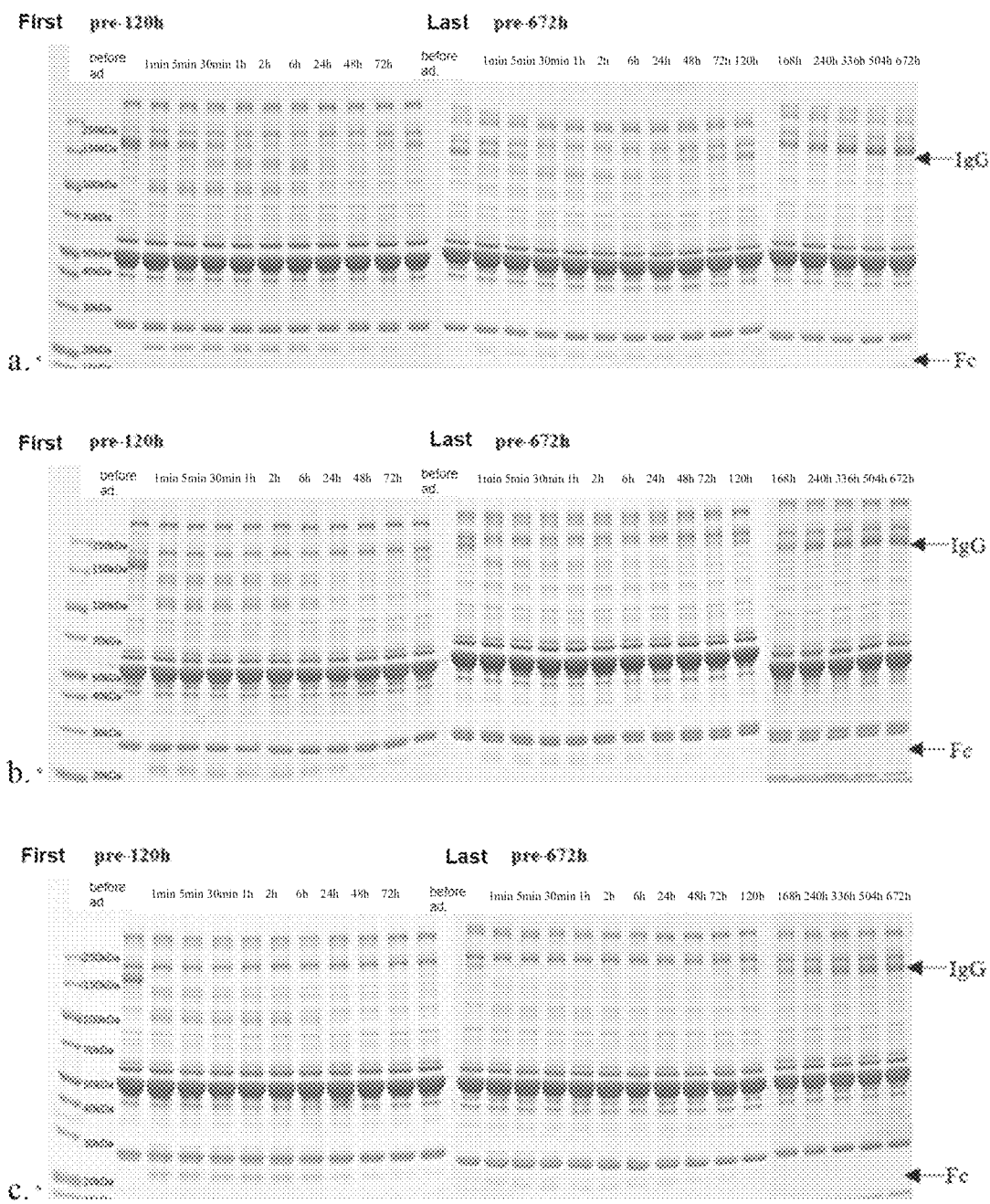
FIG. 19A shows the IgG content as a function of time (SDS-PAGE test results) in Beagle dogs injected intravenouslly with IDEEV2 once weekly for twice in each dose group; a. at a dose of 0.2 mg/kg; b. at a dose of 2 mg/kg; and c. at a dose of 20 mg/kg.
Figure 19B:
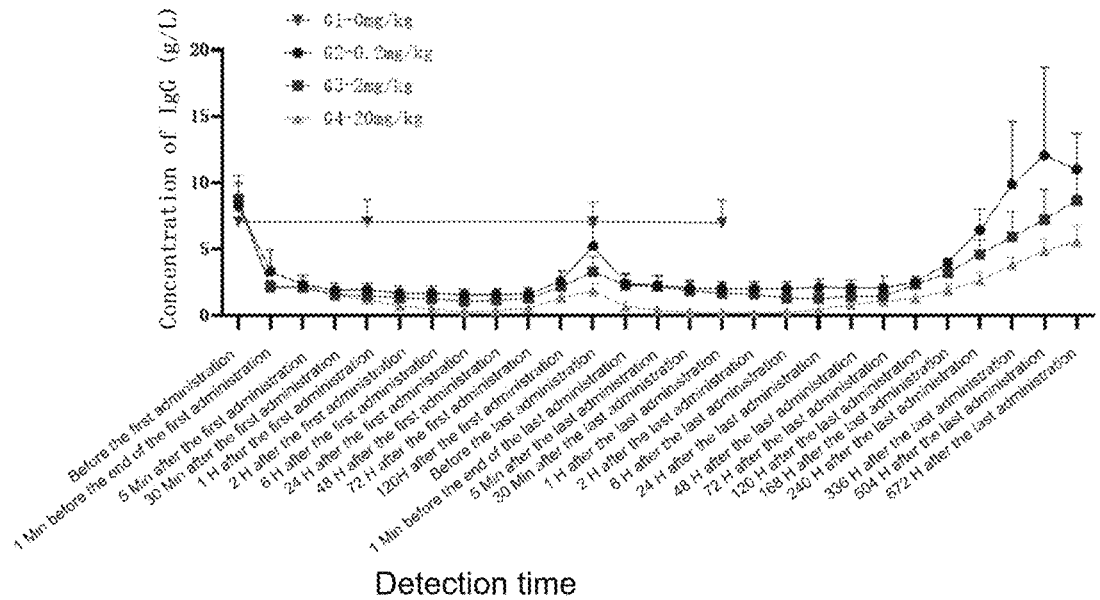
FIG. 19B shows the IgG content as a function of time (ELISA test results) in Beagle dogs injected intravenouslly with IDEEV2 once weekly for twice in each dose group.

As can be seen from the above data (FIGS. 19A and 19B), after intravenous infusion of IDEEV2 to Beagle dogs, IgG in dogs could be rapidly digested within the dose range of 0.2-20 mg/kg. Most of the IgG in dogs was digested within the first blood sample collection point (1 min before the end of administration) after IDEEV2 administration. About 3 days after administration, the content of the digested product gradually returned to the pre-dose level. There is a certain individual difference in the increase of IgG. About 10-28 days after administration, the IgG content in dogs can recover to the normal level range.

Taken together with the above data, IDEEV2 can rapidly and efficiently digest IgG in both New Zealand rabbits and Beagle dogs, demonstrating the superiority of IDEEV2 in antibody-mediated autoimmune diseases, especially in the acute severe type of life-threatening antibody-mediated autoimmune diseases.

Example 20. IDEEV2 Effectively Reverse Antiplatelet Antibody-Induced Thrombocytopenia The BALB/c mouse thrombocytopenia model was established by intraperitoneal injection of 10 mg/mouse modeling agent (rabbit IgG prepared by purification of rabbit antiserum against mouse platelets), and the pharmacodynamic effect of intravenous injection of IDEEV2 on the BALB/c mouse thrombocytopenia model was evaluated.

Figure 20A:
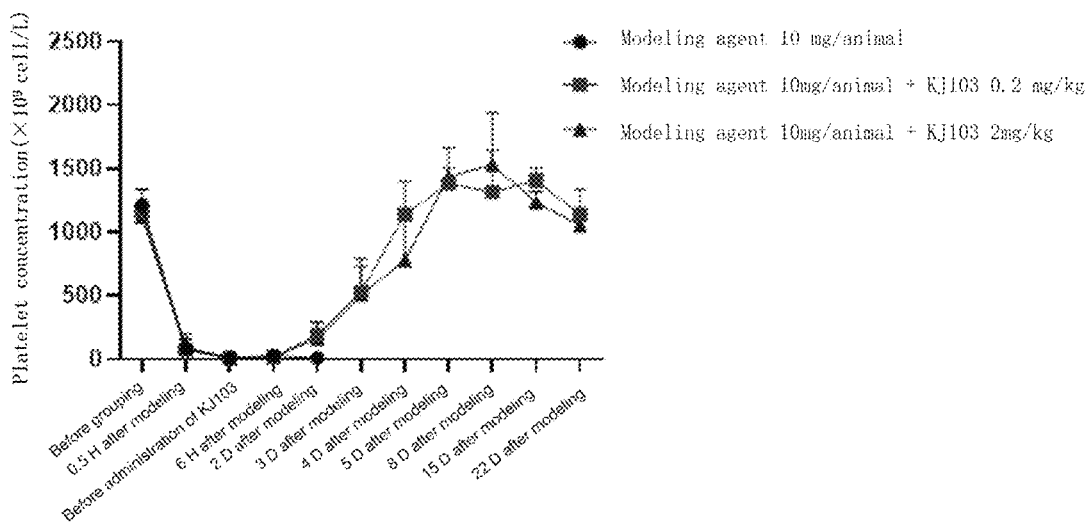
FIG. 20A shows the platelet count in antiplatelet antibody modeling animal injected intraperitoneally with IDEEV2 of each group as a function of time.
Figure 20B:
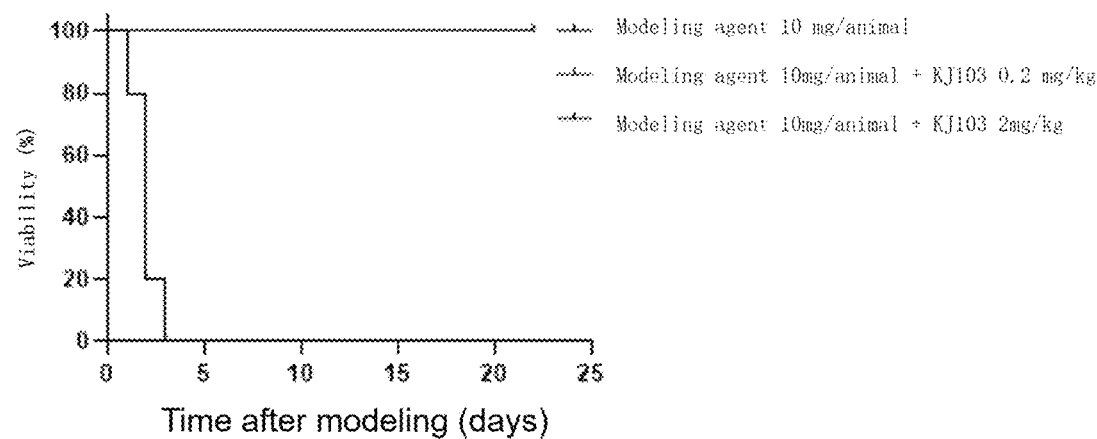
FIG. 20B shows the survival rate in antiplatelet antibody modeling animals injected intraperitoneally with IDEEV2 of each group as a function of time.

Platelet count in the model control group and IDEEV2 low and high dose groups were similar before modeling. At 0.5 h after modeling, the platelet count in each group decreased significantly. Platelet count decreased continuously in each group before IDEEV2 administration (i.e. about 2 h after modeling). After administering the modeling agent, the platelet count of the model control group animals remained consistently low (FIG. 20A), and all animals in this group died within 3 days (FIG. 20B). The platelet count of animals in IDEEV2 low and high dose groups began to recover after administration, which was similar to that before modeling at D20, indicating that IDEEV2 had significant improvement effect on thrombocytopenia in BALB/c mouse. Furthermore, the variants of the present invention have a better symptom-improving effect in autoimmune diseases caused by the anti-autoantibody.

Example 21. Immunoglobulin Degrading Enzyme Mutant Effectively Eliminates the Negative Effect of High Immunoglobulin on the Anti-Tumor Effect of Monoclonal Antibody IDEEV2 was evaluated against anti-CD38 mAb using the Daudi mouse model. The experimental design included 4 groups: 1) vehicle control group; 2) anti-CD38 monoclonal antibody daratumumab; 3) anti-CD38 monoclonal antibody daratumumab+IVIg; 4) anti-CD38 mAb daratumumab+IDEEV2+IVIg. Specifically, log phase cells were used to inoculate mouse subcutaneously, and each CB-17 SCID mouse was inoculated subcutaneously with 5×10⁶ cells of Daudi cells in the right armpit under sterile conditions, at a dose of 0.1 mL per mouse. On the day of cell inoculation, a single intraperitoneal injection of 1 g/kg IVIg was administered. After 24 hours, a single intravenous injection of 5 mg/kg of immunoglobulin degrading enzyme IDEEV2 was administered. Ten days after administration of IVIg, 2 mg/kg of anti-CD38 monoclonal antibody was administered by intraperitoneal injection, once a week, for a total of 4 times. After CD38 administration, tumor volume was measured twice a week for a total of 4 weeks.

Figure 21:
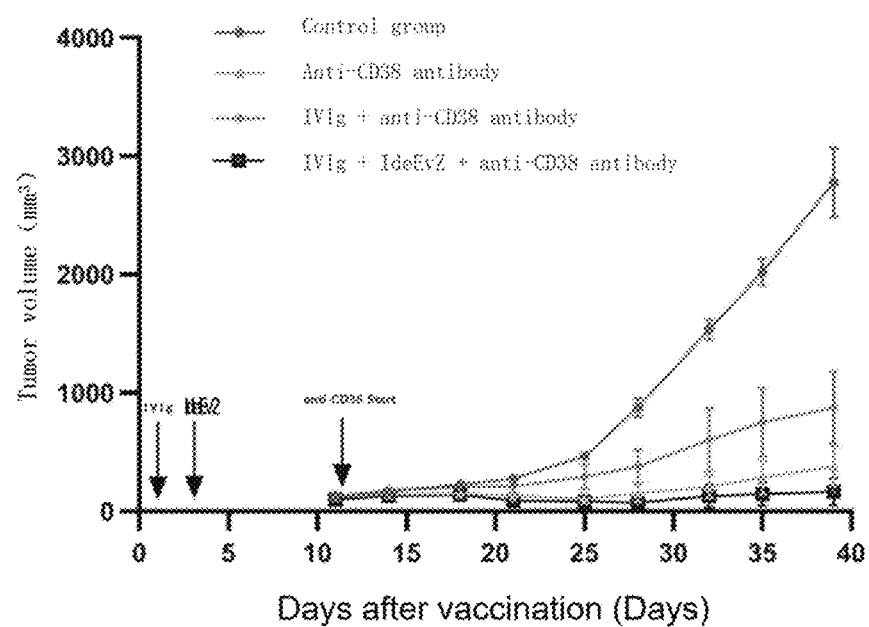
FIG. 21 shows that immunoglobulin degrading enzyme mutants can eliminate the negative effect on the antitumor effect of monoclonal antibodies.

The results of the experiment (FIG. 21) show that the presence of IgG (IVIg) inhibits the efficacy of anti-CD38 mAb in the treatment of tumors. IDEEV2 can reduce the inhibition of antibody therapeutic effect by naturally occurring IgG, and significantly enhance the therapeutic effect of therapeutic antibody.

Example 22. Effect of IgG Degrading Enzyme Mutant on AAV Infection In Vivo

C57BL/6J mouse were given a single intraperitoneal dose of IVIg (1 g/kg), and a single intravenous dose of IDEEV2 (5 mg/kg) 30 minutes after IVIg administration. AAV9-Fluc (dose 2×10¹¹ vg/animal) was administered 24 h after IVIg administration. Fluorescence imaging was performed at D8, D15, D22, D29, D36, and D43. D44, heart, and liver tissue samples were taken to detect the copy number of the Fluc gene.

1) Fluorescent control group (AAV9-Fluc);
2) Model group (IVIg+AAV9-Fluc);
3) Test article group (IVIg+IDEEV2+AAV9-Fluc).

Figure 22A:
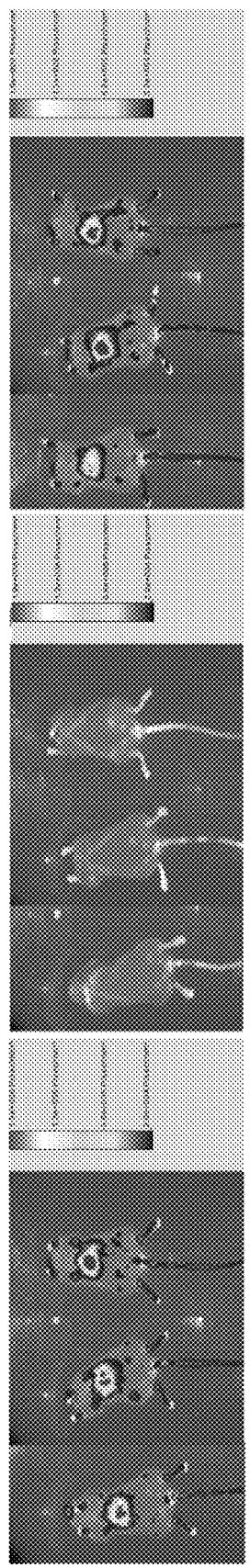
FIG. 22A shows a systemic transduction visualization of the AAV9-Fluc-infected mouse. From left to right, 1) fluorescence control group (AAV9-Fluc); 2) model group (IVIg+AAV9-Fluc); 3) test article group (IVIg+IDEEV2+AAV9-Fluc).
Figure 22B:
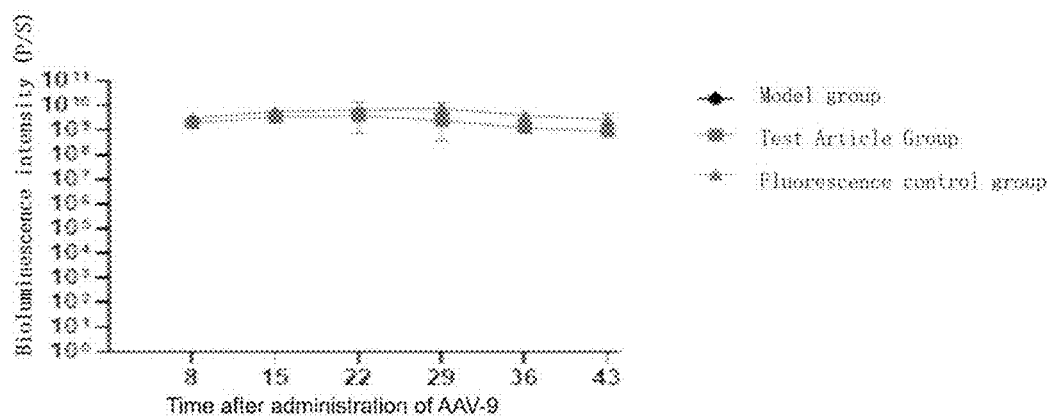
FIG. 22B shows a systemic transduction visualization of the AAV9-Fluc-infected mouse.
Figure 23:
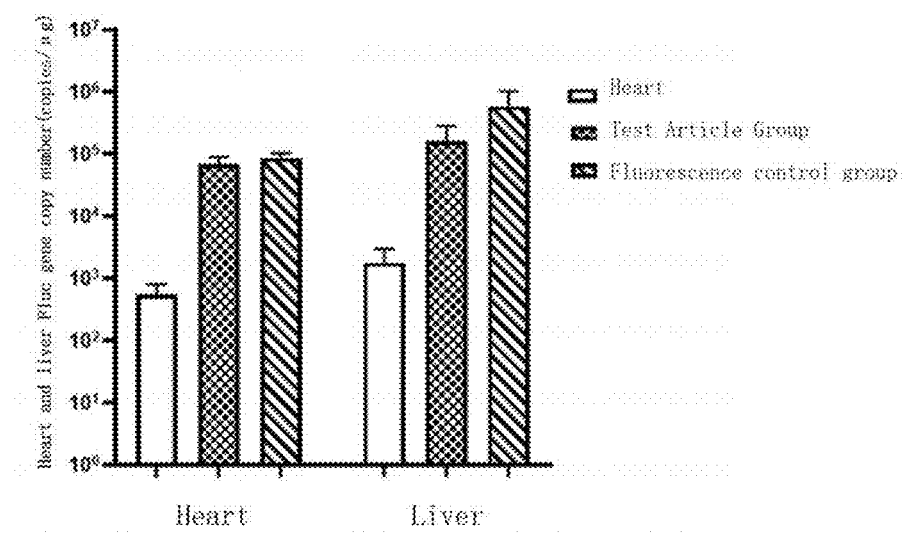
FIG. 23 shows the cardiac and hepatic transduction visualization of AAV9-Fluc-infected mouse.

The results showed that AAV had no infectious effect on mouse in the presence of IVIg, whereas IDEEV2 completely can eliminate the effect of IVIg on AAV infection (FIGS. 22A and 22B). The virus was efficiently transduced in both heart and liver tissues (FIG. 23). The results of this experiment demonstrate that the mutants of the present invention are effective in degrading human immunoglobulin G in vivo and eliminate the interference of virus-neutralizing antibodies on viral-based therapeutic carrier drugs.

The applicant declares that the present invention illustrates the detailed methods of the present invention through the above embodiments, but the present invention is not limited to the above detailed methods, which does not mean that the present invention must rely on the above detailed methods to be implemented. It will be apparent to those skilled in the art that any modifications to the present invention, equivalent alterations to the various raw materials of the products of the present invention, and additions of auxiliary components, selections of specific ways, etc. fall within the scope and disclosure of the present invention.

What is claimed is:

1. A mutant of an immunoglobulin degrading enzyme IdeE, wherein an amino acid sequence of the immunoglobulin degrading enzyme IdeE is shown as SEQ ID NO: 2:
the mutant comprises a mutation of a truncation of the immunoglobulin degrading enzyme IdeE, by deleting the sequence of the first 15, the first 16, the first 17, the first 18 or the first 19 amino acids at the N-terminus; and
the mutant comprises the amino acid sequence shown as SEQ ID NO: 36.

2. A protein comprising the mutant of claim 1 and a signal peptide at an N-terminal of the mutant.

3. A composition, comprising: the mutant of claim 1; and, a pharmaceutically acceptable carrier or excipient.

4. The composition of claim 3, further comprising an antibody.

5. The composition of claim 4, wherein a target of the antibody is selected from the group consisting of a cell surface protein, a cytokine, a hormone, an enzyme, an intracellular messenger, an intercellular messenger, and an immune checkpoint.

6. A composition, comprising: the protein of claim 2; and, a pharmaceutically acceptable carrier or excipient.

7. The composition of claim 6, further comprising: an antibody.

8. The composition of claim 7, wherein a target of the antibody is selected from the group consisting of a cell surface protein, a cytokine, a hormone, an enzyme, an intracellular messenger, an intercellular messenger, and an immune checkpoint.

9. The composition of claim 6, further comprising: a viral vector drug.

10. The composition of claim 9, wherein, the viral vector drug is selected from the group consisting of an oncolytic virus, a gene therapy virus, and a viral vector vaccine.

11. The composition of claim 6, further comprising: a drug capable of reducing a level of an IgG in a blood.

12. The composition of claim 11, wherein the drug capable of reducing the level of the IgG in the blood is selected from the group consisting of an FcRn antibody and an Fc fragment variant with a high affinity to FcRn.

13. A kit comprising: a first kit or a second kit:
the first kit comprising:
(1) the mutant of claim 1; and,
(2) (a) a pharmaceutically acceptable carrier or excipient and (b) an antibody; and,
the second kit comprising: a third kit and a fourth kit, wherein
the third kit comprises the mutant of claim 1,
the fourth kit comprising:
(1) a pharmaceutically acceptable carrier or excipient;
(2) an antibody.

14. A kit comprising: a first kit or a second kit:
the first kit comprising:
(1) the protein of claim 2; and,
(2) (a) a pharmaceutically acceptable carrier or excipient and (b) an antibody; and,
the second kit comprising: a third kit and a fourth kit, wherein
the third kit comprises the protein of claim 2,
the fourth kit comprising:
(1) a pharmaceutically acceptable carrier or excipient;
(2) an antibody.

* * * * *